United States Patent
Linnemann et al.

(10) Patent No.: US 10,690,658 B2
(45) Date of Patent: Jun. 23, 2020

(54) MEANS AND METHODS FOR DETERMINING T CELL RECOGNITION

(71) Applicants: AIMM Therapeutics B.V., Amsterdam Zuidoost (NL); Stichting Het Nederlands Kanker Instituut-Antoni van Leeuwenhoek Ziekenhuis, Amsterdam (NL)

(72) Inventors: Carsten Linnemann, Amsterdam (NL); Laura Bies, Amsterdam (NL); Marit Martha van Buuren, Amsterdam (NL); Antonius Nicolaas Maria Schumacher, Amsterdam (NL); Hergen Spits, Amsterdam Zuidoost (NL); Remko Schotte, Amsterdam Zuidoost (NL)

(73) Assignees: AIMM THERAPEUTICS B.V., Amsterdam (NL); STICHTING HET NEDERLANDS KANKER INSTITUUT-ANTONI VAN LEEUWENHOEK ZIEKENHUIS, Amsterdam (NL)

(*) Notice: Subject to any disclaimer, the term of this patent is extended or adjusted under 35 U.S.C. 154(b) by 153 days.

(21) Appl. No.: 15/316,419

(22) PCT Filed: Jun. 5, 2015

(86) PCT No.: PCT/NL2015/050405
§ 371 (c)(1),
(2) Date: Dec. 5, 2016

(87) PCT Pub. No.: WO2015/187018
PCT Pub. Date: Dec. 10, 2015

(65) Prior Publication Data
US 2017/0160269 A1    Jun. 8, 2017

(30) Foreign Application Priority Data

Jun. 5, 2014    (EP) .................... 14171396

(51) Int. Cl.
*C12N 5/00*   (2006.01)
*C12N 5/02*   (2006.01)
*G01N 33/50*   (2006.01)
*A61K 39/00*   (2006.01)
*G01N 33/569*   (2006.01)

(52) U.S. Cl.
CPC ...... *G01N 33/5052* (2013.01); *A61K 39/0011* (2013.01); *G01N 33/505* (2013.01); *G01N 33/56977* (2013.01)

(58) Field of Classification Search
None
See application file for complete search history.

(56) References Cited

U.S. PATENT DOCUMENTS

| | | | |
|---|---|---|---|
| 6,982,326 B1 * | 1/2006 | Griffith | C07K 14/415 435/320.1 |
| 2010/0113745 A1 | 5/2010 | Spits et al. | |
| 2012/0157662 A1 | 6/2012 | Beaumont et al. | |
| 2013/0085260 A1 | 4/2013 | Lapointe et al. | |

FOREIGN PATENT DOCUMENTS

WO    WO2007067046 A1    6/2007

OTHER PUBLICATIONS

Schultze et al ( J Clin Invest. 1997, v. 100, pp. 2757-2765).*
Schultze et al., "CD40-activated Human B Cells: An Alternative Source of Highly Efficient Antigen Presenting Cells to Generate Autologous Antigen-specific T Cells for Adoptive Immunotherapy," J. Clin. Invest., The American Society for Clinical Investigation, Inc., vol. 100, No. 11, Dec. 1997, pp. 2757-2765.
Falini et al., "Bcl-6 protein expression in normal and neoplastic lymphoid tissues," Annals of Oncology 8 (Supp. 2), S101-S104, 1997.
Mathew et al., "A negative feedback loop mediated by the Bc16-cullin 3 complex limits Tfh cell differentiation," The Rockefeller University Press, J. Exp. Med. 2014, vol. 211, No. 6, pp. 1137-1151.
Rosenberg et al., "Durable Complete Responses in Heavily Pretreated Patients with Metastatic Melanoma Using T-Cell Transfer Immunotherapy," Clin. Cancer Res. 2011, 17:4550-4557.
Tran et al., "Cancer Immunotherapy Based on Mutation-Specific CD4+ T Cells in a Patient with Epithelial Cancer," Science, vol. 344, May 9, 2014, pp. 641-645.
Alexandrov et al., "Signatures of mutational processes in human cancer," Nature, vol. 500, pp. 415-421, Aug. 22, 2013.
Vogelstein et al., "Cancer Genome Landscapes," Science 339, pp. 1546-1558, (2013), DOI: 10.1126/science.1235122.
Robbins et al., "Mining exomic sequencing data to identify mutated antigens recognized by adoptively transferred tumor-reactive T cells," Nature Medicine, vol. 19, No. 6, Jun. 2013, pp. 747-752.
van Rooij et al., "Tumor Exome Analysis Reveals Neoantigen-Specific T-Cell Reactivity in an Ipilimumab-Responsive Melanoma," Journal of Clinical Oncology, vol. 31, No. 32, Nov. 10, 2013, pp. e439-e442.
Lu et al., "Mutated PPP1R3B Is Recognized by T Cells Used to Treat a Melanoma Patient Who Experienced a Durable Complete Tumor Regression," J. Immunol. 2013, 190:6034-6042, May 20, 2013.
Wick et al., "Surveillance of the Tumor Mutanome by T Cells during Progression from Primary to Recurrent Ovarian Cancer," Clin. Cancer Res., 20(5), pp. 1125-1134, © 2013 American Association for Cancer Research.
Friedman et al., "Tumor-specific CD4+ Melanoma Tumor-infiltrating Lymphocytes," J. Immunother., vol. 35, No. 5, Jun. 2012, pp. 400-408.
Kitano et al. "Enhancement of Tumor-Reactive Cytotoxic CD4+ T-cell Responses after Ipilimumab Treatment in Four Advanced Melanoma Patients," Cancer Immunol. Res., 1(4), pp. 235-244, © 2013 American Association for Cancer Research.

(Continued)

*Primary Examiner* — Michail A Belyavskyi
(74) *Attorney, Agent, or Firm* — Hoffmann & Baron, LLP

(57) ABSTRACT

The invention provides improved screening methods for testing T cell recognition of T cell epitopes.

30 Claims, 16 Drawing Sheets
Specification includes a Sequence Listing.

(56) References Cited

OTHER PUBLICATIONS

Varela et al., "Exome sequencing identifies frequent mutation of the SWI/SNF complex gene PBRM1 in renal carcinoma," Nature, vol. 469, Jan. 27, 2011, pp. 539-542.
Kenter et al., "Vaccination against HPV-16 Oncoproteins for Vulvar Intraepithelial Neoplasia," The New England Journal of Medicine, Nov. 5, 2009, 361:1838-47.
Ossendorp et al., "Specific T Helper Cell Requirement for Optimal Induction of Cytotoxic T Lymphocytes against Major Histocompatibility Complex Class II Negative Tumors," J. Exp. Med. © The Rockefeller University Press, vol. 187, No. 5, Mar. 2, 1998, pp. 693-702.
Champiat et al., "Exomics and Immunogenics," 2014, OncoImmunology, 3:1, e27817, DOI: 10.4161/onci.27817.
Dudley et al., "Cancer Regression and Autoimmunity in Patients After Clonal Repopulation with Antitumor Lymphocytes," Science, Oct. 25, 2002, pp. 850-854.
Kwakkenbos et al., "Genetic manipulation of B cells for the isolation of rare therapeutic antibodies from the human repertoire," Methods, vol. 65, Jan. 1, 2014, pp. 38-43.
Quezada et al., "Tumor-reactive CD4+ T cells develop cytotoxic activity and eradicate large established melanoma after transfer into lymphopenic hosts," J. Exp. Med., vol. 207, No. 3, pp. 637-650.
Kwakkenbos et al., "Generation of stable monoclonal antibody-producing B cell receptor-positive human memory B cells by genetic programming," Nature Medicine, vol. 16, No. 1, Jan. 2010, pp. 123-128.
Kessels et al., "The Impact of Self-Tolerance on the Polyclonal CD8+ T Cell Repertoire," J. Immunol. 2004, 172:2324-2331.
Calis et al., "Properties of MHC Class I Presented Peptides That Enhance Immunogenicity," PLOS Computational Biology, Oct. 2013, vol. 9, Issue 10, e1003266, pp. 1-13.
Verdegaal et al., "Successful treatment of metastatic melanoma by adoptive transfer of blood-derived polyclonal tumor-specific CD4+ and CD8+ T cells in combination with low-dose interferon-alpha," Cancer Immunol. Immunother. (2011), 60:953-963.
Li et al., "Fast and accurate short read alignment with Burrows-Wheeler transform," Bioinformatics Original Paper, vol. 25, No. 14, 2009, pp. 1754-1760.
DePristo et al., "A framework for variation discovery and genotyping using next-generation DNA sequencing data," Nature Genetics, vol. 43, No. 5, May 2011, pp. 491-498.
Larson et al., "SomaticSniper: identification of somatic point mutations in whole genome sequencing data," Bioinformatics Original Paper, vol. 28, No. 3, 2012, pp. 311-317.
Li et al., "The Sequence Alignment/Map format and SAMtools," Bioinformatics Applications Note, vol. 25, No. 16, 2009, pp. 2078-2079.
Cingolani et al., "A program for annotating and predicting the effects of single nucleotide polymorphisms, SnpEff: SNPs in the genome of *Drosophila melanogaster* strain w1118; iso-2; iso-3," Fly, vol. 6, Issue 2, pp. 80-92, Apr./May/Jun. 2012.
Trapnell et al., "TopHat: discovering splice junctions with RNA-Seq," Bioinformatics Original Paper, vol. 25, No. 9, 2009, pp. 1105-1111.
Trapnell et al., "Transcrpt assembly and quantification by RNA-Seq reveals unannotated transcripts and isoform switching during cell differentiation," Nature Biotechnology, vol. 28, No. 5, May 2010, pp. 511-515.
Linnemann et al., "High-throughput identification of antigen-specific TCRs by TCR gene capture," Nature Medicine, vol. 19, No. 11, Nov. 2013, pp. 1534-1541.
Riddell et al., "Principles for Adoptive T Cell Therapy of Human Viral Diseases", Annu. Rev. Immunol., 13:545-86 (1995).
Roosnek et al., "Kinetics of MHC-Antigen Complex Formation on Antigen-Presenting Cells", Journal of Immunology, 140:4079-4082 (1988).
Riddell et al., "CD8+Cytotoxic T Cell Therapy of Cytomegalovirus and HIV Infection", Current Opinion in Immunology, 5:484-491 (1993).

\* cited by examiner

Figure 2

| | Mutational load # somatic mutations | Synonymous mutations | Non-synonymous mutations | RNA expressed, non-synonymous |
|---|---|---|---|---|
| NKIRTIL018 | 322 | 93 | 229 | 188 |
| NKIRTIL045 | 180 | 55 | 125 | 99 |
| NKIRTIL034 | 464 | 152 | 312 | 173 |
| NKIRTIL027 | 1393 | 484 | 909 | 582 |
| B0 | 1243 | 432 | 811 | 501 |

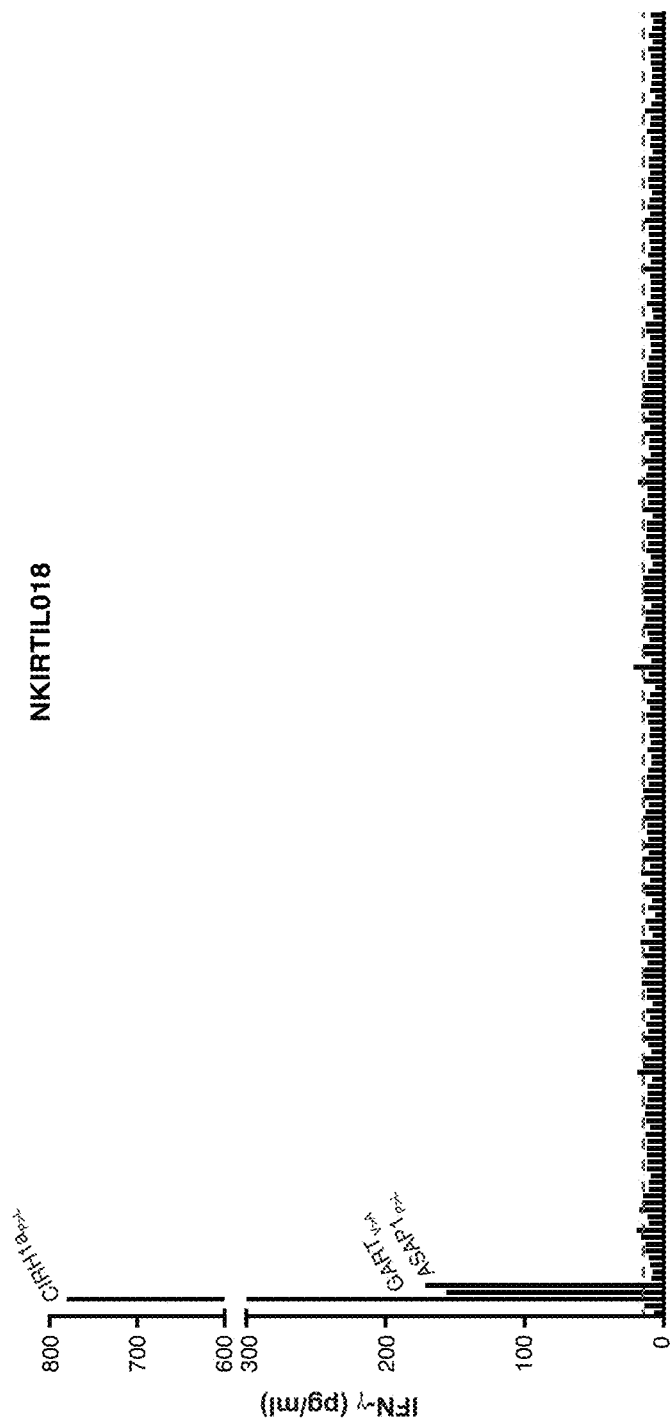

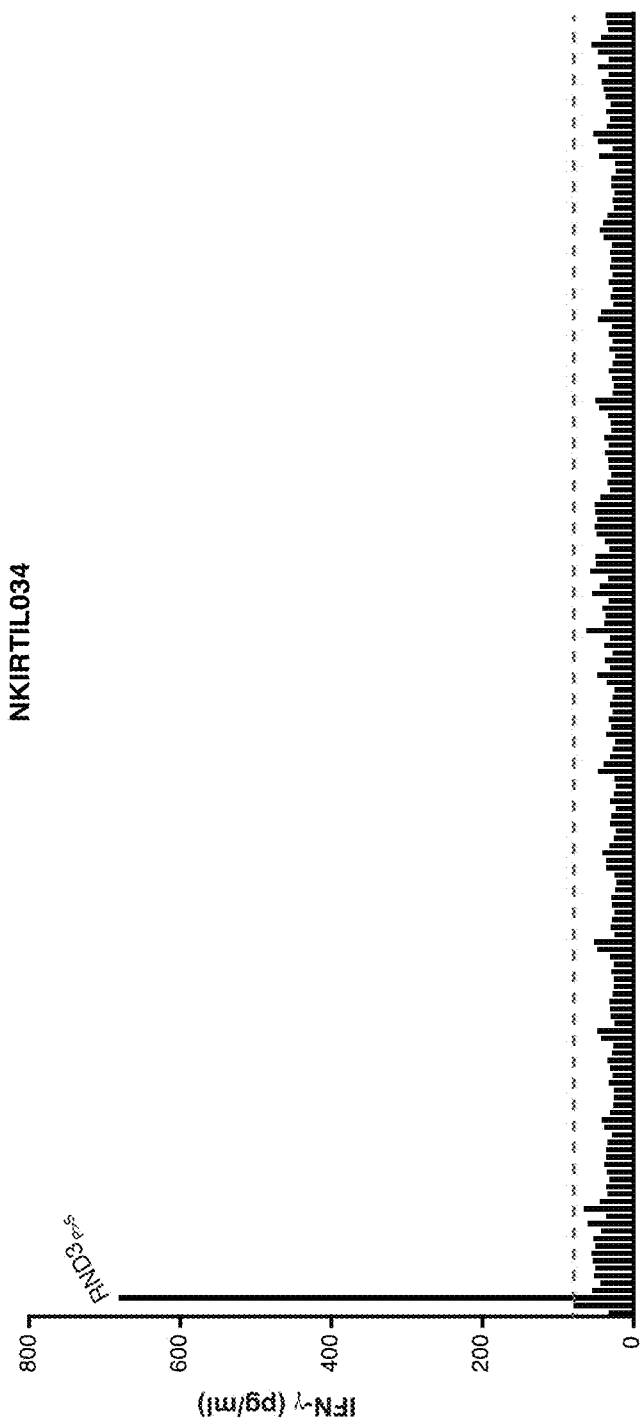

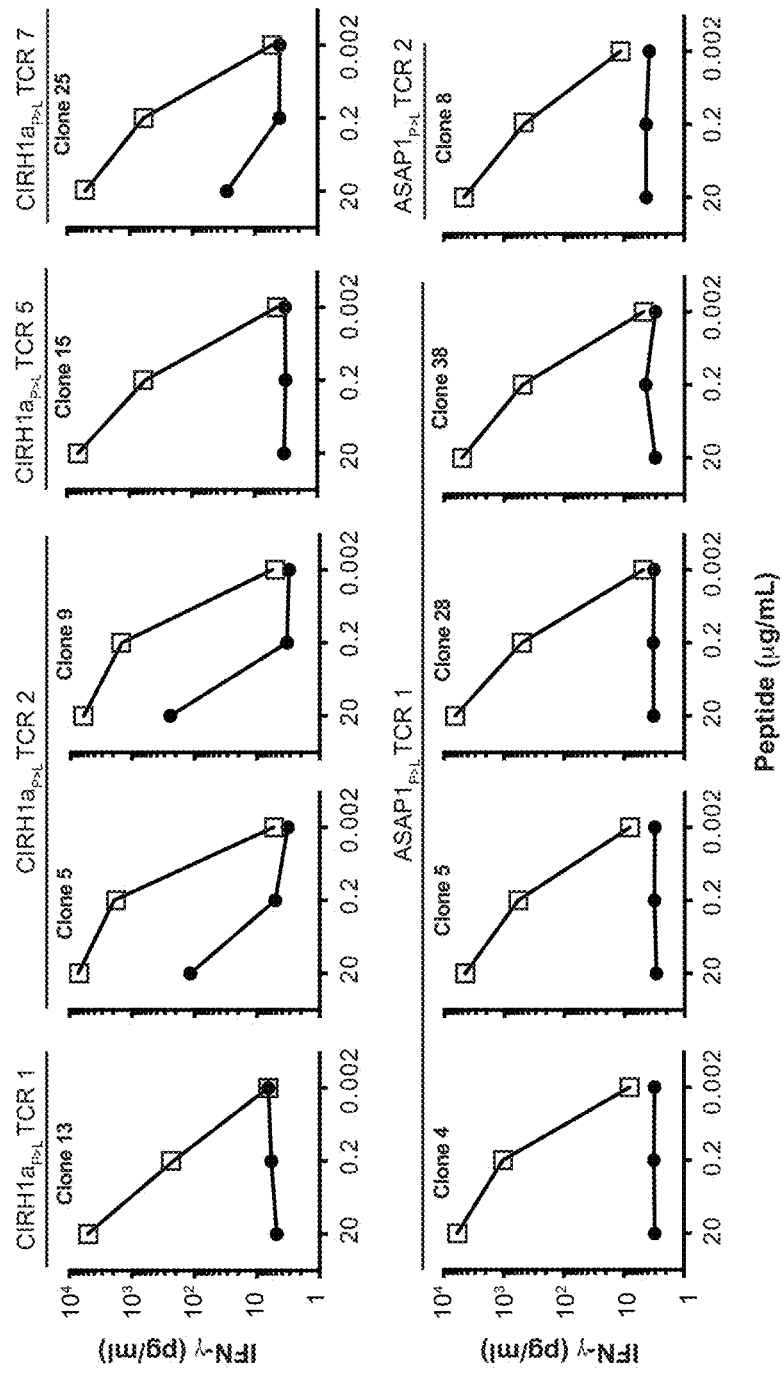

Figure 11
2015 01 13 – The use of AIMM immortalized B cells
for CD8 neo-antigen identification.
a) CBA based approach – initial screen
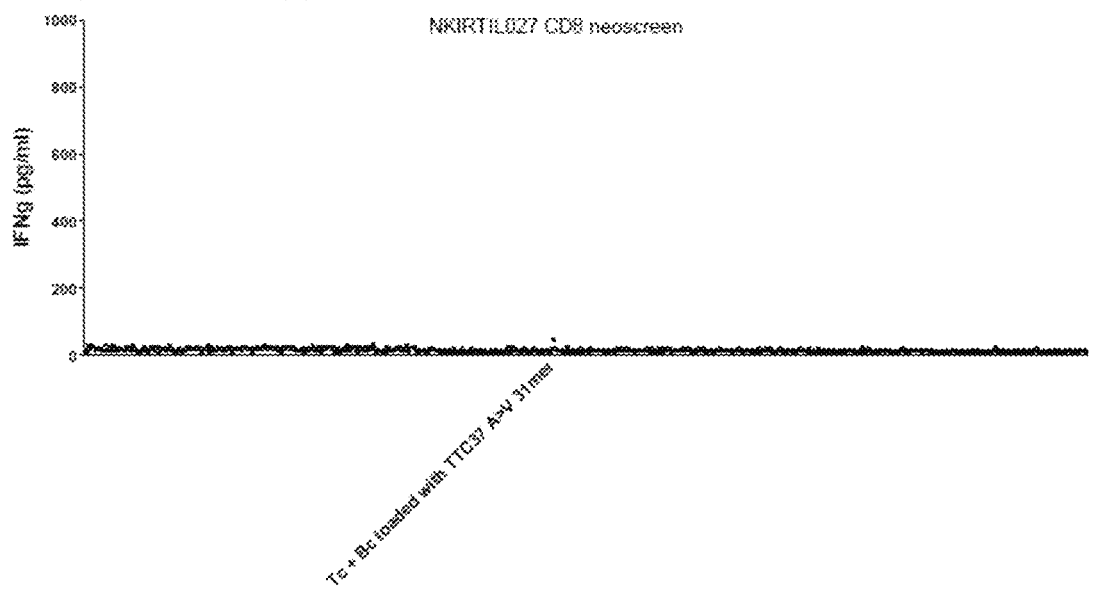
b) CBA based approach
independent confirmation
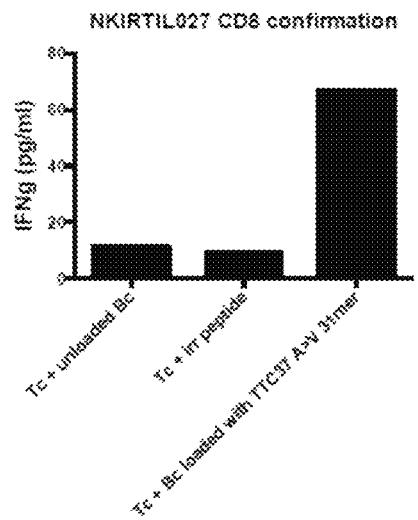
c) Multimer based approach
TTC37 A>V 9mer HLA-A*01:01 restricted
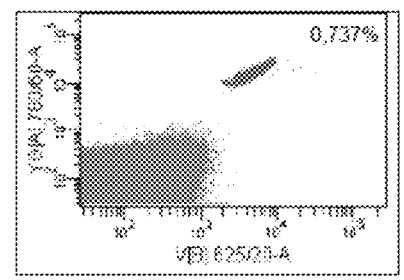

SEQUENCE LISTING

```
<160> NUMBER OF SEQ ID NOS: 28

<210> SEQ ID NO 1
<211> LENGTH: 64
<212> TYPE: DNA
<213> ORGANISM: Artificial Sequence
<220> FEATURE:
<223> OTHER INFORMATION: IDT-DNA oligonucleotide
<220> FEATURE:
<221> NAME/KEY: misc_feature
<222> LOCATION: (35)..(40)
<223> OTHER INFORMATION: n is a, c, g, or t

<400> SEQUENCE: 1
agatcggaag agcacacgtc tgaactccag tcacnnnnnn atctcgtatg ccgtcttctg      60
cttg                                                                  64

<210> SEQ ID NO 2
<211> LENGTH: 64
<212> TYPE: DNA
<213> ORGANISM: Artificial Sequence
<220> FEATURE:
<223> OTHER INFORMATION: IDT-DNA oligonucleotide
<220> FEATURE:
<221> NAME/KEY: misc_feature
<222> LOCATION: (25)..(30)
<223> OTHER INFORMATION: n is a, c, g, or t

<400> SEQUENCE: 2
caagcagaag acggcatacg agatnnnnnn gtgactggag ttcagacgtg tgctcttccg      60
atct                                                                  64

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
aatgatacgg cgaccaccga gatct                                           25
```

```
<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
caagcagaag acggcatacg ag                                              22

<210> SEQ ID NO 5
<211> LENGTH: 13
<212> TYPE: PRT
<213> ORGANISM: Artificial Sequence
<220> FEATURE:
<223> OTHER INFORMATION: CIRH1AP>L

<400> SEQUENCE: 5

Arg Lys Ile Thr Phe Leu His Arg Cys Leu Ile Ser Cys
1               5                   10

<210> SEQ ID NO 6
<211> LENGTH: 19
<212> TYPE: PRT
<213> ORGANISM: Artificial Sequence
<220> FEATURE:
<223> OTHER INFORMATION: ASAP1P>L

<400> SEQUENCE: 6

Lys Pro Pro Pro Gly Asp Leu Pro Leu Lys Pro Thr Glu Leu Ala Pro
1               5                   10                  15

Lys Pro Gln

<210> SEQ ID NO 7
<211> LENGTH: 31
<212> TYPE: PRT
<213> ORGANISM: Artificial Sequence
<220> FEATURE:
<223> OTHER INFORMATION: mutated petide variant

<400> SEQUENCE: 7

Glu Val Lys Asn Tyr Asp Ala Ala Leu Arg Lys Ile Thr Phe Leu His
1               5                   10                  15

Arg Cys Leu Ile Ser Cys Ser Lys Lys Arg Gln Leu Leu Leu Phe
            20                  25                  30

<210> SEQ ID NO 8
<211> LENGTH: 28
<212> TYPE: PRT
<213> ORGANISM: Artificial Sequence
<220> FEATURE:
<223> OTHER INFORMATION: mutated petide variant

<400> SEQUENCE: 8

Glu Val Lys Asn Tyr Asp Ala Ala Leu Arg Lys Ile Thr Phe Leu His
1               5                   10                  15

Arg Cys Leu Ile Ser Cys Ser Lys Lys Arg Gln Leu
            20                  25

<210> SEQ ID NO 9
<211> LENGTH: 25
<212> TYPE: PRT
<213> ORGANISM: Artificial Sequence
<220> FEATURE:
<223> OTHER INFORMATION: mutated petide variant
```

```
<400> SEQUENCE: 9

Glu Val Lys Asn Tyr Asp Ala Ala Leu Arg Lys Ile Thr Phe Leu His
1               5                   10                  15

Arg Cys Leu Ile Ser Cys Ser Lys Lys
            20                  25

<210> SEQ ID NO 10
<211> LENGTH: 22
<212> TYPE: PRT
<213> ORGANISM: Artificial Sequence
<220> FEATURE:
<223> OTHER INFORMATION: mutated petide variant

<400> SEQUENCE: 10

Glu Val Lys Asn Tyr Asp Ala Ala Leu Arg Lys Ile Thr Phe Leu His
1               5                   10                  15

Arg Cys Leu Ile Ser Cys
            20

<210> SEQ ID NO 11
<211> LENGTH: 19
<212> TYPE: PRT
<213> ORGANISM: Artificial Sequence
<220> FEATURE:
<223> OTHER INFORMATION: mutated petide variant

<400> SEQUENCE: 11

Glu Val Lys Asn Tyr Asp Ala Ala Leu Arg Lys Ile Thr Phe Leu His
1               5                   10                  15

Arg Cys Leu

<210> SEQ ID NO 12
<211> LENGTH: 15
<212> TYPE: PRT
<213> ORGANISM: Artificial Sequence
<220> FEATURE:
<223> OTHER INFORMATION: mutated petide variant

<400> SEQUENCE: 12

Glu Val Lys Asn Tyr Asp Ala Ala Leu Arg Lys Ile Thr Phe Leu
1               5                   10                  15

<210> SEQ ID NO 13
<211> LENGTH: 17
<212> TYPE: PRT
<213> ORGANISM: Artificial Sequence
<220> FEATURE:
<223> OTHER INFORMATION: mutated petide variant

<400> SEQUENCE: 13

Leu His Arg Cys Leu Ile Ser Cys Ser Lys Lys Arg Gln Leu Leu Leu
1               5                   10                  15

Phe

<210> SEQ ID NO 14
<211> LENGTH: 19
<212> TYPE: PRT
<213> ORGANISM: Artificial Sequence
<220> FEATURE:
<223> OTHER INFORMATION: mutated petide variant

<400> SEQUENCE: 14

Thr Phe Leu His Arg Cys Leu Ile Ser Cys Ser Lys Lys Arg Gln Leu
1               5                   10                  15
```

Leu Leu Phe

<210> SEQ ID NO 15
<211> LENGTH: 22
<212> TYPE: PRT
<213> ORGANISM: Artificial Sequence
<220> FEATURE:
<223> OTHER INFORMATION: mutated petide variant

<400> SEQUENCE: 15

```
Arg Lys Ile Thr Phe Leu His Arg Cys Leu Ile Ser Cys Ser Lys Lys
1               5                   10                  15

Arg Gln Leu Leu Leu Phe
            20
```

<210> SEQ ID NO 16
<211> LENGTH: 25
<212> TYPE: PRT
<213> ORGANISM: Artificial Sequence
<220> FEATURE:
<223> OTHER INFORMATION: mutated petide variant

<400> SEQUENCE: 16

```
Ala Ala Leu Arg Lys Ile Thr Phe Leu His Arg Cys Leu Ile Ser Cys
1               5                   10                  15

Ser Lys Lys Arg Gln Leu Leu Leu Phe
            20                  25
```

<210> SEQ ID NO 17
<211> LENGTH: 28
<212> TYPE: PRT
<213> ORGANISM: Artificial Sequence
<220> FEATURE:
<223> OTHER INFORMATION: mutated petide variant

<400> SEQUENCE: 17

```
Asn Tyr Asp Ala Ala Leu Arg Lys Ile Thr Phe Leu His Arg Cys Leu
1               5                   10                  15

Ile Ser Cys Ser Lys Lys Arg Gln Leu Leu Leu Phe
            20                  25
```

<210> SEQ ID NO 18
<211> LENGTH: 31
<212> TYPE: PRT
<213> ORGANISM: Artificial Sequence
<220> FEATURE:
<223> OTHER INFORMATION: mutated petide variant

<400> SEQUENCE: 18

```
Leu Ala Glu Leu Pro Gln Lys Pro Pro Gly Asp Leu Pro Leu Lys
1               5                   10                  15

Pro Thr Glu Leu Ala Pro Lys Pro Gln Ile Gly Asp Leu Pro Pro
            20                  25                  30
```

<210> SEQ ID NO 19
<211> LENGTH: 28
<212> TYPE: PRT
<213> ORGANISM: Artificial Sequence
<220> FEATURE:
<223> OTHER INFORMATION: mutated petide variant

<400> SEQUENCE: 19

```
Leu Ala Glu Leu Pro Gln Lys Pro Pro Gly Asp Leu Pro Leu Lys
1               5                   10                  15
```

Pro Thr Glu Leu Ala Pro Lys Pro Gln Ile Gly Asp
            20                  25

<210> SEQ ID NO 20
<211> LENGTH: 25
<212> TYPE: PRT
<213> ORGANISM: Artificial Sequence
<220> FEATURE:
<223> OTHER INFORMATION: mutated petide variant

<400> SEQUENCE: 20

Leu Ala Glu Leu Pro Gln Lys Pro Pro Pro Gly Asp Leu Pro Leu Lys
1               5                   10                  15

Pro Thr Glu Leu Ala Pro Lys Pro Gln
            20                  25

<210> SEQ ID NO 21
<211> LENGTH: 22
<212> TYPE: PRT
<213> ORGANISM: Artificial Sequence
<220> FEATURE:
<223> OTHER INFORMATION: mutated petide variant

<400> SEQUENCE: 21

Leu Ala Glu Leu Pro Gln Lys Pro Pro Pro Gly Asp Leu Pro Leu Lys
1               5                   10                  15

Pro Thr Glu Leu Ala Pro
            20

<210> SEQ ID NO 22
<211> LENGTH: 19
<212> TYPE: PRT
<213> ORGANISM: Artificial Sequence
<220> FEATURE:
<223> OTHER INFORMATION: mutated petide variant

<400> SEQUENCE: 22

Leu Ala Glu Leu Pro Gln Lys Pro Pro Pro Gly Asp Leu Pro Leu Lys
1               5                   10                  15

Pro Thr Glu

<210> SEQ ID NO 23
<211> LENGTH: 15
<212> TYPE: PRT
<213> ORGANISM: Artificial Sequence
<220> FEATURE:
<223> OTHER INFORMATION: mutated petide variant

<400> SEQUENCE: 23

Leu Ala Glu Leu Pro Gln Lys Pro Pro Pro Gly Asp Leu Pro Leu
1               5                   10                  15

<210> SEQ ID NO 24
<211> LENGTH: 17
<212> TYPE: PRT
<213> ORGANISM: Artificial Sequence
<220> FEATURE:
<223> OTHER INFORMATION: mutated petide variant

<400> SEQUENCE: 24

Leu Lys Pro Thr Glu Leu Ala Pro Lys Pro Gln Ile Gly Asp Leu Pro
1               5                   10                  15

Pro

```
<210> SEQ ID NO 25
<211> LENGTH: 19
<212> TYPE: PRT
<213> ORGANISM: Artificial Sequence
<220> FEATURE:
<223> OTHER INFORMATION: mutated petide variant

<400> SEQUENCE: 25

Leu Pro Leu Lys Pro Thr Glu Leu Ala Pro Lys Pro Gln Ile Gly Asp
1               5                   10                  15

Leu Pro Pro

<210> SEQ ID NO 26
<211> LENGTH: 22
<212> TYPE: PRT
<213> ORGANISM: Artificial Sequence
<220> FEATURE:
<223> OTHER INFORMATION: mutated petide variant

<400> SEQUENCE: 26

Pro Gly Asp Leu Pro Leu Lys Pro Thr Glu Leu Ala Pro Lys Pro Gln
1               5                   10                  15

Ile Gly Asp Leu Pro Pro
            20

<210> SEQ ID NO 27
<211> LENGTH: 25
<212> TYPE: PRT
<213> ORGANISM: Artificial Sequence
<220> FEATURE:
<223> OTHER INFORMATION: mutated petide variant

<400> SEQUENCE: 27

Lys Pro Pro Pro Gly Asp Leu Pro Leu Lys Pro Thr Glu Leu Ala Pro
1               5                   10                  15

Lys Pro Gln Ile Gly Asp Leu Pro Pro
            20                  25

<210> SEQ ID NO 28
<211> LENGTH: 28
<212> TYPE: PRT
<213> ORGANISM: Artificial Sequence
<220> FEATURE:
<223> OTHER INFORMATION: mutated petide variant

<400> SEQUENCE: 28

Leu Pro Gln Lys Pro Pro Pro Gly Asp Leu Pro Leu Lys Pro Thr Glu
1               5                   10                  15

Leu Ala Pro Lys Pro Gln Ile Gly Asp Leu Pro Pro
            20                  25
```

MEANS AND METHODS FOR DETERMINING T CELL RECOGNITION

The invention relates to the fields of biology and medicine.

T cell responses play an important role in the mammalian immune system. For instance, CD8+ cytotoxic T cells (CTL) play an important role in combating pathogen-infected cells and tumor cells. Immune responses are also elicited by CD4+ helper T cells, via the production of multiple effector cytokines such as for instance interferon gamma (typically abbreviated as IFN-γ or IFNg), tumor necrosis factor alpha (TNF-α) and interleukin 2 (IL-2), that activate CTL and induce maturation of antibody producing B cells. Adoptive cell therapy, which is increasingly explored for tumor treatment, makes use of T cell responses that occur in vivo. During this therapy, tumor-specific T cells are isolated from a patient and cultured ex vivo. Subsequently, the tumor-specific T cells are reintroduced into the patient, preferably after chemotherapy-induced lymphodepletion in order to eliminate immunoregulatory cells, resulting in an increased anti-tumor response. For instance, Rosenberg et al. 2011 describe treatment of metastatic melanoma patients with the adoptive transfer of autologous CD8+ CTL-containing tumor infiltrating lymphocytes (TILs) in conjunction with IL-2. High response rates were observed and in this study 22% of the melanoma patients achieved a complete tumor regression. Tran et al. 2014 describe immunotherapy of epithelial cancer. CD4+ T cells were obtained from a patient and incubated with autologous dendritic cells (DCs) which presented peptides with tumor-specific mutations. AT cell clone specific for one tumor-specific mutation was found, and infusion of these T cells into the patient resulted in tumor regression and prolonged stabilization of disease.

Dendritic cells are professional antigen presenting cells (APCs), which are specifically adapted for presenting antigen in the context of major histocompatibility complex I or II (MHC-I or MHC-II). Therefore, DCs are cells of first choice for presenting T cell epitopes and identifying T cells with a desired specificity. However, mature DCs cannot be expanded in long term cultures, so that monocytes have to be obtained freshly from a large volume of blood or from the bone marrow of an individual and a short-lived DC culture has to be prepared each time before a given T cell selection procedure can be performed. This is time consuming, expensive and involves significant discomfort to the individual.

It is an object of the invention to provide optimized methods for determining whether T cells recognize T cell epitopes.

Accordingly, one aspect of the invention provides a method for determining whether a T cell recognizes a T cell epitope, comprising:
  inducing, enhancing and/or maintaining expression of BCL6 in at least one B cell;
  inducing, enhancing and/or maintaining expression of an anti-apoptotic nucleic acid in said at least one B cell;
  allowing expansion of said at least one B cell into a B cell culture;
  incubating B cells of said B cell culture with at least one compound;
  incubating the resulting B cells with T cells; and
  determining whether at least one T cell recognizes at least one T cell epitope of said at least one compound.

One interesting application of a method according to the invention is a screening assay for T cell epitopes. In this embodiment, first an in vitro B cell culture is obtained. Subsequently, B cells from this culture are used as antigen presenting cells by incubating them with test compounds that are potential T cell epitopes or that encode for potential T cell epitopes, so that the potential T cell epitopes are displayed at the B cell surface in the context of MHCs. Subsequently, the loaded B cells are incubated with T cells in order to test whether the T cells recognize any of the potential T cell epitopes. This is for instance tested by determining whether the T cells are bound to any of the test epitopes. Preferably. T cell activation is measured. Various ways of determining T cell activation are known in the art, such as for instance testing whether the T cells produce cytokines, or testing whether the T cells proliferate. If tumor-specific T cells are searched for, interferon gamma release is preferably measured because many tumor-specific T cells produce IFNg. If a test epitope is recognized by T cells, it is then typically selected for further research, for instance for the development of an immunogenic composition or vaccine, and/or for eliciting or boosting a T cell response against a disease associated with the presence of that epitope. In one embodiment, such T cell response is elicited or boosted in vivo, by administration of the epitope to an individual who is suffering from, or at risk of suffering from, a disease which is associated with the presence of said epitope, such as for instance cancer or a pathogenic infection. Alternatively, a T cell response against a T cell epitope that has been identified with a method according to the invention is elicited in vitro, preferably using T cells from an individual who is suffering from, or at risk of suffering from, a disease which is associated with the presence of said epitope, where after the T cells are cultured and subsequently administered to the individual as a medicament or prophylactic agent against said disease.

Another application of a method according to the invention is a screening assay for the presence of T cells against a known T cell epitope. In this embodiment, B cells from the above-mentioned B cell culture are incubated with one or more known T cell epitopes. Again, the T cell epitopes are displayed at the B cell surface in the context of MHCs. Subsequently, the epitope-loaded B cells are incubated with T cells from a sample in order to test whether that sample contains T cells that recognize one or more of the T cell epitopes. If this appears to be the case, it can for instance be concluded that (at least one of) the individual(s) from which the sample was obtained exhibits a T cell response in vivo against at least one of the tested T cell epitopes. This may for instance mean that a certain treatment or vaccination procedure has been successful.

As used herein, a T cell epitope means an amino acid sequence that has the capability of being bound by MHC molecules and recognized by T cells, such as for instance by CD8+ CTL or CD4+ helper T cells.

A compound as used in the present invention typically comprises amino acid residues or a nucleic acid sequence encoding for amino acid residues. Said compound is preferably a protein or a (poly)peptide or a nucleic acid molecule comprising a nucleic acid sequence encoding a protein or a (poly)peptide. The compound typically either comprises one or more known T cell epitopes, or it is tested for the presence of one or more T cell epitopes. Preferably, said compound is a protein or a (poly)peptide.

As used herein, the term "amino acid" embraces natural amino acids as well as non-natural, or artificial, amino acids.

As used herein, the terms "nucleic acid molecule" and "nucleic acid sequence" refers to a chain of nucleotides, preferably DNA or RNA. In other embodiments a nucleic acid molecule comprises other kinds of nucleic acid structures such as for instance a DNA/RNA helix, peptide nucleic acid (PNA), locked nucleic acid (LNA) and/or a ribozyme.

As used herein, a T cell "recognizes" a T cell epitope if it specifically binds to said epitope in the context of MHC. This means that said T cell preferentially binds said epitope over other antigens. A T cell typically binds a T cell epitope via its T cell receptor (TCR). Non-specific binding, or sticking, of T cells to a certain compound is not embraced by the term "recognizing".

The term "incubating" B cells with a compound or with T cells means that the B cells are exposed to the compound or T cells for a sufficiently long time to allow an interaction between the B cells and the compound or T cells to take place. Typically, if said compound is a peptide, the incubation time can be considerably shorter then the incubation time for proteins. Proteins first need to be processed by the B cells before protein-derived peptides are displayed at the surfaces of the B cells, whereas peptides can typically directly bind the B cell's MHC molecules without the need for internalization and processing. In one embodiment, B cells are incubated with peptides for about 15-25 hours, preferably for about 18-24 hours. Subsequently, peptide-loaded B cells are preferably incubated with T cells for about 5-50 hours, preferably for about 6-48 hours. If said compound is a nucleic acid molecule encoding a protein or (poly)peptide, the B cells are transduced or transfected with said nucleic acid molecule resulting in the translation of said nucleic acid molecule and intracellular production of said encoded protein or (poly)peptide. Transduction or transfection of B cells with nucleic acid molecules can be achieved with method commonly known in the art. Such methods include, but are not limited to, viral vector particle-mediated transduction, microinjection, and standard nucleic acid transfection methods such as those based on calcium phosphate precipitation, liposomes, polycations, magnetofection and electroporation.

An important advantage of a method according to the present invention is the fact that an in vitro B cell culture is used that can be maintained for a prolonged period of time, which includes weeks, months or even years. Each time that APCs are needed, B cells can be taken from such B cell culture for a screening assay. Hence, B cells only once need to be harvested from an individual, where after they remain in culture and remain available for subsequent assays. This is an important advantage over the use of dendritic cells.

Furthermore, a method according to the invention allows the detection of T cell epitope recognition with a high sensitivity, because the inventors have surprisingly discovered that with a method of the invention T cell activation towards epitopes other than the test epitopes (background signals or background noise) is particularly low. This is for instance in contrast with the results when Epstein Barr Virus (EBV) immortalized B cells are used as antigen presenting cells. For instance, in FIG. 4 it is very difficult to establish which of the dots (T cell activation using EBV-immortalized B cells as APCs) are relevant due to the high level of background signals. On the other hand, T cell activation signals obtained with a method according to the present invention (triangles) are clearly detectable as a result of the low (or even absent) background noise. Hence, a method according to the present invention provides a much more accurate and sensitive screening method for T cell epitopes, since background signaling is so low that relevant T cell epitopes immediately become apparent, even when the signal is weak. Such weak signals can for instance be caused by a rather low extent of T cell activation, or a low number of epitope-recognizing T cells might be present in the assay. In existing methods of the prior art wherein EBV immortalized B cells are used, many relevant signals are missed because they cannot be distinguished from the large background noise whereas in a method according to the present invention, relevant T cell epitopes are better detected.

The particularly good results and low background noise obtained with a method according to the invention are surprising, because B cells are used that are cultured in vitro for a prolonged period of time. These B cells remain in a "plasmablast-like state", meaning that the in vitro B cells are capable of both replicating and antibody production. In a natural situation, plasmablasts are only short lived in vivo. Antibody is typically produced by B cells that have differentiated into plasma cells, which have lost their capability of proliferating. The long term "plasmablast-like cultures" that are used in the present invention are therefore unique cells that do not exist in nature. These cells have non-natural properties. For instance, their size is larger as compared to natural in vivo plasmablasts and they highly express co-stimulatory molecules like CD40. CD80, CD86, ICOSL. When such non-natural B cells are incubated with T cells, background noise was therefore to be expected. However, surprisingly, the methods according to the present invention involve such low background noise that a very sensitive assay has become possible.

Hence, the very low level of background noise is surprising, since in vitro cultured B cells are used, which are present in a non-natural environment and have undergone non-natural treatment, which affects the characteristics of the B cells. Moreover, in a preferred embodiment the B cells contain one or more exogenous nucleic acid molecules, which often contain a non-natural detectable label such as for instance green fluorescent protein. The resulting in vitro B cells are, therefore, different from their natural counterparts and were expected to activate T cells, independently from the administered epitopes of the test assay. Yet, with a method according to the invention, background noise is surprisingly avoided to such extent that a very sensitive test assay has become available. A method according to the present invention is, therefore, preferred over existing prior art methods because it allows very sensitive, accurate and straightforward screening assays for T cell recognition of T cell epitopes, using B cells that are long-lived and only need to be obtained once from an individual. Repeated harvesting of monocytes and differentiation of these cells into DCs is no longer necessary, which reduces processing times, costs and the extent of discomfort of the individual.

A further advantage of a method according to the invention is that the long-term "plasmablast-like" B cells which are used in the assay are larger than their natural counterparts in vivo. This means that more MHC is present at the surface of the B cells, so that a larger number of epitopes can be displayed. This also increases the sensitivity of the assays of the present invention.

B cells have been used as antigen presenting cells before. For instance, Schultze et al. describe a method wherein CD40-activated B cells are used as APCs for presenting a melanoma-derived peptide to T cells from healthy individuals in order to generate melanoma-specific T cells. The generation of antigen-specific T cells by incubating T cells from healthy individuals with a T cell epitope does, however, not involve the above-mentioned sensitivity concerns. Screening methods according to the present invention are particularly advantageous when the detection of low concentrations of T cells of interest is at stake.

Various kinds of compounds are suitable for use in a screening method according to the invention. For instance, proteins may be used, which are internalized by the B cells, processed and peptide fragments are subsequently displayed at their surface. If a T cell binds such peptide and becomes activated, it is concluded that said protein comprises a T cell epitope that is recognized by the T cell.

In a preferred embodiment, the B cells are incubated with peptides. This provides the advantage that at least some of the peptides are directly bound to the surface MHCs of the B cells, so that internal processing by the B cells is not necessary for these peptides. This enables faster epitope presentation and, hence, shorter assay times. Although the cultured B cells of the present invention will typically already display peptides at their surface in complex with MHCs, many of these MHC-bound peptides are easily replaced by the administered peptides, resulting in MHC-test peptide complexes, that are subsequently tested for T cell activation.

In order to enable efficient T cell recognition, said peptides preferably have a length of between 5 and 40 amino acids, preferably between 5 and 35 amino acids, more preferably between 8 and 35 amino acids or between 9 and 31 amino acids or between 10 and 31 amino acids or between 11 and 31 amino acids or between 8 and 20 amino acids or between 9 and 20 amino acids or between 10 and 20 amino acids or between 11 and 20 amino acids or between 8 and 15 amino acids or between 8 and 12 amino acids or between 8 and 11 amino acids, enabling efficient MHC binding and surface presentation. As is well known by the skilled person, T cell epitopes presented by MHC class I typically have a length of between 8 and 11 amino acids, whereas T cell epitopes presented by MHC class II typically have a length of between 11 and 20 amino acids. Therefore, test peptides with similar lengths are advantageous since this facilitates MHC binding. However, as shown in the examples, longer peptides are also suitable for testing potential T cell epitopes. Such longer peptides are either internalized and processed by the B cells, or directly bound to MHC. MHC-II is particularly well capable of binding and presenting larger peptides. Hence, longer peptides are particularly suitable for testing CD4+ T cell epitope recognition.

As used herein, numerical ranges include the upper and lower values of that range. Accordingly, the term "peptide with a length of between x and y amino acids" embraces peptides with a length of x amino acids and peptides with a length of y amino acids, as well as peptides with a length in between these values.

Alternatively, a nucleic acid molecule comprising a nucleic acid sequence encoding a protein or (poly)peptide can be used. In that case, B cells are transduced or transfected with said nucleic acid molecule resulting in the translation of said nucleic acid sequence and intracellular production of said encoded protein or (poly)peptide. Fragments of such proteins and such peptides are, optionally after processing by the B cells, displayed at the B cell surface.

In order to be able to test T cell recognition of different test epitopes, said B cells are preferably incubated with different kinds of peptides, or with nucleic acid molecules comprising nucleic acid sequences encoding different kinds of peptides, preferably with at least 2, at least 3 or at least 4 different peptides or encoding nucleic acid sequences, preferably peptides. In a further embodiment, said B cells are incubated with at least 5, at least 6, at least 7, at least 8, at least 9 or with at least 10 different peptides or encoding nucleic acid sequences, preferably peptides. In order to be able to distinguish between the different epitopes, B cells are preferably present at spatially addressable positions. At each position, one or more compounds are administered to the B cells. If T cell recognition appears to be present at a certain position, it can be determined which epitope is recognized. In one embodiment several protein or peptide mixtures are used. For instance, B cells are present in different wells and each well is incubated with a different protein/peptide mixture. If in one well T cell recognition appears to take place, the proteins and/or peptides of the mixture of that particular well are typically subsequently tested individually, in order to determine which epitope(s) is/are recognized. If no T cell recognition is present in a certain well, the whole mixture that was administered to that well can be disregarded.

T cell recognition of a T cell epitope can be measured in various ways known in the art. One preferred method is measurement of T cell activation. Upon recognition of an epitope, T cells typically become activated which is for instance measurable by determining the extent of interferon gamma release. Hence, in one embodiment of the invention it is determined whether T cells have recognized at least one epitope by determining whether said T cells are activated, preferably by measuring cytokine release by the T cells. In one embodiment, interferon gamma release is measured.

In one embodiment, compound-loaded B cells (preferably protein-loaded, peptide-loaded, or nucleic acid molecule-loaded B cells) according to the invention are incubated with CD8+ CTL. In a further embodiment, compound-loaded B cells according to the invention are incubated with CD4+ helper T cells.

CD8+ CTL play an important role in combating tumor cells, as well as cells that are infected by a pathogen. Typically, the specificity of CD8+ CTL can be tested using non-cellular peptide-MHC-I complexes, such as for instance peptide-MHC-I multimers as described in Davis et al., 2011. Peptide-MHC multimers are used because the affinity of the T cell receptor (TCR) for peptide-loaded MHCs is so low that a single peptide-MHC complex would not be able to bind a T cell with sufficient strength for performing a test assay. As described in Davis et al., 2011, MHC multimers, typically tetramers, with ultraviolet (UV)-sensitive peptides, which are developed by one of the current inventors, are preferably used. These UV-sensitive peptides are cleaved by UV light, where after the resulting MHC multimers are loaded with test peptides and used for T cell binding assays.

Although peptide-MHC multimers provide a good tool for performing CD8+ T cell binding assays, these multimers are not always suitable. For instance, with peptide-MHC multimers, only the binding of T cells to test peptides can be determined. The biologic activity of these T cells, such as for instance activation, is not tested with these multimers. Moreover, MHC multimers are not available for each MHC allele. Therefore, if a certain individual appears to express MHC alleles that are not commonly present in the population, multimers of these uncommon MHC alleles will typically not be available. In such case, the binding characteristics of such individual's T cells cannot be measured with existing MHC multimers.

Hence, when the biologic activity of CD8+ T cells is to be investigated, or when T cells from an individual with uncommon MHC-I alleles are tested, peptide-MHC multimers are typically unsuitable. The methods according to the present invention, wherein B cells are used as APCs for the T cells, are therefore preferred.

Furthermore, a method according to the invention is also preferred for testing CD4+ T cells. In vivo, CD4+ helper T cells elicit anti-pathogenic and antitumor responses via the production of multiple effector cytokines, which activate CTL and induce maturation of antibody producing B cells. For adoptive cell therapy of a cancer patient, tumor infiltrating lymphocytes (TILs) are preferably used. Typically, in TILs the proportion of CD4+ T cells is higher than the proportion of CD8+ CTL. Therefore, investigation of CD4+ T cell epitopes is an important application for adoptive cell therapy. The use of CD4+ cells is advantageous, since this provides an effective T cell response whereas the need for lymphodepletion is diminished as compared to the use of CD8+ CTLs. The use of a CD4+ T cell epitope in a medicament or vaccine is also advantageous, since such medicament or vaccine will typically elicit an effective immune response in an individual. Determination of CD4+ T cell epitope recognition is, therefore, a preferred embodiment. However, the production of MHC class II multimers with UV sensitive, exchangeable peptides is more difficult than the production of peptide-MHC-I multimers, because MHC-II molecules have a peptide-binding site that, is composed of two different polypeptides, as opposed to MHC-I molecules whose peptide-binding site is composed of only one polypeptide. Since peptide-MHC-II multimers are not commonly available, and also in view of the fact that peptide-MHC-II multimers cannot be used for determining T cell activation, and in view of the fact that MHC-II is expressed on certain kinds of cells only, a method according to the invention wherein B cells are used as APCs for testing CD4+ T cell epitope recognition is a particularly preferred embodiment.

One particular embodiment provides a method according to the invention wherein said at least one B cell and said T cells are from the same human individual. This embodiment is particularly advantageous if T cell recognition of certain epitopes is tested with the aim of using the T cells as a medicament against a certain disorder. One interesting application is adoptive cell therapy. A patient suffering from a disease often exhibits an immune response against the disease. In case of cancer, such immune response is typically directed against protein mutations that are present in the tumor, but not in the original healthy tissue of the individual, so that the mutations are recognized as non-self. Such mutations are referred to herein as "tumor-specific mutations" or "tumor-specific amino acid sequences" (although the same kind of amino acid sequence may occur in other diseases or pathogens as well) and the resulting antigen is typically referred to as a "modified self antigen". Furthermore, a "disease-specific T cell epitope" is defined herein as a T cell epitope whose presence in an individual is associated with disease. A disease-specific T cell epitope for instance comprises a T ell epitope from a surface protein of a pathogen. The same kind of T cell epitope may occur in various diseases or pathogens, but is typically not—or to a significantly lower extent—present in healthy tissue of the individual.

An individual's immune response is, however, often not sufficient to combat the disease, for instance due to escape mechanisms and/or immunoregulatory cells. In such case. T cells from the patient are preferably tested with a method according to the invention. When B cells from the same patient are used, background signals are further reduced because autologous B cells are less immunogenic for the T cells as compared to allogeneic B cells. For adoptive cell therapy, B cells from a patient are thus preferably incubated with compounds that comprise or encode disease-specific T cell epitopes, such as tumor-specific or pathogen-specific amino acid sequences, and T cell recognition is tested using T cells from the same patient.

T cells recognizing such disease-specific epitope are preferably expanded in vitro and subsequently administered to the patient, which will for instance result in an anti-tumor or anti-pathogen T cell response. Alternatively, or additionally, a disease-specific T cell epitope that is recognized by a patient's T cells is administered to the patient in order to boost his/her immune system, resulting in an enhanced immune response. Such disease-specific T cell epitope may be administered as such, or as part of a larger complex such as for instance an oligopeptide, protein, epitope-carrier complex, or epitope-MHC complex. In one embodiment, such disease-specific T cell epitope is bound to an antigen-presenting cell, preferably a B cell from a B cell culture as prepared in a method according to the present invention. Administration of such APCs will elicit or boost an anti-tumor response in vivo.

One preferred embodiment provides a method according to the invention, wherein said T cell epitope is from a modified self-antigen. Said T cell epitope preferably comprises a tumor-specific amino acid sequence. Said tumor may be any kind of tumor. Preferred examples are melanoma, epithelial cancer, lung squamous cell carcinoma, lung adenocarcinoma, stomach cancer, esophagus cancer, lung small cell carcinoma, colorectal cancer, bladder cancer, uterine cancer, cervical cancer, liver cancer, head and neck cancer, kidney clear cell cancer, B cell lymphoma, kidney papillary cancer, breast cancer, pancreas cancer, myeloma, ovary cancer, prostate cancer, glioblastoma, glioma, neuroblastoma, medulloblastoma, CLL, chromphobe renal cell carcinoma, thyroid cancer, ALL, AML and pilocytic astrocytoma. Preferably, said T cell epitope is a melanoma-specific epitope or an epithelial cancer-specific epitope. Also provided is a method according to the invention, wherein the B cells are incubated with T cells from an individual suffering from, or having suffered from, cancer, preferably melanoma or epithelial cancer.

Another preferred embodiment provides a method according to the invention wherein said T cell epitope is a from a non-self antigen, preferably from a pathogen. Said pathogen is preferably a virus, a bacterium or a parasite, since these pathogens typically raise a cell-mediated immune response in vivo. In one embodiment, for instance, in order to develop a T cell vaccine against a certain pathogen, peptides are produced based on the sequence of surface proteins of said pathogen. B cells from a B cell culture as described herein are incubated with these peptides and, subsequently, with T cells. Preferably, T cells are used that are from an individual who has been exposed to said pathogen before, so that memory T cells will be present. If one or more test peptides appear to be recognized by T cells, these peptides are candidates for a vaccine against said pathogen. Again, the sensitivity of such screening method according to the present invention is important.

Also provided is therefore a method according to the invention, wherein the B cells are incubated with T cells from an individual suffering from, or having suffered from, a pathogen, preferably a virus, a bacterium or a parasite.

Another preferred embodiment provides a method according to the invention wherein said T cell epitope is from an autoantigen. This means that such T cell epitope is present in proteins (or nucleic acid) that naturally occur in an individual, wherein the epitope is normally tolerated by an individual's immune system but wherein the epitope is recognized by the immune system of an individual suffering from an autoimmune disease. Non-limiting examples of such autoimmune diseases include diabetes type I (immune response against insulin-producing pancreatic cells), multiple sclerosis (immune response against the insulating covers of nerve cells) and coeliac disease, wherein exposure to gluten protein causes the immune system to cross-react with small intestine tissue. In some embodiments, screening methods according to the present invention are used in order to determine whether a sample comprises T cells that recognize an autoantigen. For instance, B cells wherein the expression of Bcl-6 and Bcl-xL have been induced, enhanced and/or maintained are incubated with one or more autoantigens (or peptides derived thereof), where after T cell epitopes will be displayed at the surface of the B cells. Subsequently, the B cells are incubated with T cells from a sample. If one or more T cell epitopes appear to be bound by T cells from said sample, it is concluded that said sample comprises T cells that recognize an autoantigen. Such sample is then typically typed as being specific for a certain autoimmune disease. In some embodiments, this result is subsequently used for determining whether an individual from which the sample has been obtained is suffering from, or at risk of suffering from, an autoimmune disease.

In some embodiments, a screening assay according to the invention is performed in order to test for potential autoimmune T cell epitopes. According to these embodiments, B cells wherein the expression of Bcl-6 and Bcl-xL have been induced, enhanced and/or maintained are incubated with one or more test compounds, preferably peptides, where after the peptide-loaded B cells are incubated with T cells from an autoimmune patient. Peptides that appear to be bound by these T cells are subsequently selected, for instance for further autoimmunity research.

Also provided is therefore a method according to the invention, wherein the B cells are incubated with T cells from an individual suffering from, or having suffered from, an autoimmune disease, preferably multiple sclerosis, diabetes or coeliac disease.

As used herein, a T cell epitope "from" a modified self-antigen, or "from" a non-self antigen or "from" an autoantigen means a T cell epitope sequence, wherein said sequence is also present on, or in, said modified self-antigen or non-self antigen or autoantigen, respectively. Said T cell epitope could for instance be a peptide obtained from said antigen (for instance via internalization and processing of an antigen by a B cell, where after a T cell epitope is presented at the B cell's surface in the context of MHC) or said T cell epitope could be artificially produced, for instance using a recombinant cellular peptide production platform or a chemical peptide synthesizer. Hence, a T cell epitope "from" a certain antigen does not need to be physically obtained from said antigen. Instead, once the sequence of such T cell epitope is known, said T ell epitope may be separately produced. Said T cell epitope preferably comprises a peptide. In some embodiments, said T cell epitope is part of a protein or polypeptide or other proteinaceous compound.

As used herein, the term "B cell" means a B cell that has been obtained from an individual, or a B cell that originates from such B cell. Said individual is preferably a mammal, such as for instance a human, mouse, rat, rabbit, ape, monkey, cow, sheep, dog or cat. In one preferred embodiment, said individual is a human individual or a rabbit. An example of B cells originating from an individual's B cell is the progeny of a B cell from an individual, that is formed in vitro after one or more cell division cycles. Such progeny for instance includes an ex vivo B cell culture.

An ex vivo B cell culture is a culture that contains B cells and/or progeny thereof. Other kinds of cells may also be present in the culture. For instance, B cell stimulator cells such as CD40 positive L cells and/or EL4B5 cells are typically also present in a B cell culture used in the invention. Additionally, other kinds of cells, which were also present in a sample from an individual from which the B cells were obtained, could still be present in a B cell culture. When present in B cell culturing conditions, such non-B cells are typically less capable of proliferating as compared to B cells, so that the number of such contaminating cells will typically decline in time. Preferably, at least 70% of the cells of a B cell culture are B cells. More preferably, at least 75%, 80%, 85%, 90% or 95% of the cells of said B cell culture are B cells. In one embodiment, B cells and B cell stimulator cells such as CD40 positive L cells and/or EL4B5 cells are essentially the only kinds of cell present in a B cell culture as used in the invention. In some embodiments, essentially all cells of said B cell culture are B cells.

Bcl-6 encodes a transcriptional repressor which is required for normal B cell and T cell development and maturation and which is required for the formation of germinal centers. Bcl-6 is highly expressed in germinal center B cells whereas it is hardly expressed in plasma cells. Bcl-6 inhibits differentiation of activated B cells into plasma cells. In a method according to the invention, Bcl-6 expression product remains present in the B cells of an ex vivo culture. The presence of Bcl-6 expression product, together with the presence of an anti-apoptotic nucleic acid, prolongs the replicative life span of the B cells. Expression of Bcl-6 is preferably induced, enhanced or maintained by administering a Bcl-6 expression-promoting compound to the original B cell(s) used for culturing, or by culturing B cells in the presence of such compound.

Further provided is therefore a method according to the invention, wherein expression of Bcl-6 in said at least one B cell is induced, enhanced and/or maintained by:
providing said B cell with a compound capable of directly or indirectly enhancing expression of Bcl-6; and/or
culturing said B cell in the presence of a compound capable of directly or indirectly enhancing expression of Bcl-6.

As used herein, the term "Bcl-6" also embraces homologues thereof, such as Bcl-6 homologues that are present in non-human mammals.

Various compounds capable of directly or indirectly enhancing expression of Bcl-6 are known in the art. Such compound for instance comprises a Signal Transducer of Activation and Transcription 5 (STAT5) protein, or a functional part or a functional derivative thereof, and/or a nucleic acid sequence coding therefore. STAT5 is a signal transducer capable of enhancing Bcl-6 expression. There are two known forms of STAT5, STAT5a and STAT5b, which are encoded by two different, tandemly linked genes. Administration and/or activation of STAT5, or a homologue thereof, results in enhanced levels of Bcl-6. Hence, STAT5, or a homologue thereof, or a functional part or a functional derivative thereof, is capable of directly increasing expression of Bcl-6. Provided is therefore a method according to the invention, comprising:
inducing, enhancing and/or maintaining expression of STAT5 in at least one B cell;
inducing, enhancing and/or maintaining expression of an anti-apoptotic nucleic acid in said at least one B cell;
allowing expansion of said at least one B cell into a B cell culture;
incubating B cells of said B cell culture with at least one compound;
incubating the resulting B cells with T cells; and
determining whether at least one T cell recognizes at least one T cell epitope of said at least one compound. Also provided is a method according to the invention, wherein expression of Bcl-6 in said at least one B cell is induced, enhanced and/or maintained by providing said B cell with STAT5, or with a homologue thereof, or with a functional part or a functional derivative thereof. Alternatively, or additionally, expression of Bcl-6 in said at least one B cell is induced, enhanced and/or maintained by providing said B cell with a nucleic acid molecule encoding STAT5, or a homologue thereof, or a functional part or a functional derivative thereof, or by culturing said B cell in the presence of STAT5, or in the presence of a homologue, or functional part, or functional derivative thereof.

The presence of STAT5 directly increases the amount of Bcl-6. It is also possible to indirectly increase expression of Bcl-6. This is for instance done by regulating the amount of a certain compound, which in turn is capable of directly or indirectly activating STAT5, or a homologue thereof, and/or increasing expression of STAT5, or expression of a homologue thereof. Hence, in one embodiment the expression and/or activity of endogenous and/or exogenous STAT5, or the expression of a homologue thereof, is increased.

As used herein, the term "homologue" of, for instance, Bcl-6 or STAT5 or Blimp-1 means a mammalian protein corresponding to Bcl-6 or STAT5 or Blimp-1, respectively, which means that it has a corresponding, similar function in non-human B cells as compared to the function of Bcl-6 or STAT5 or Blimp-1 in human B cells.

It is preferred to provide a B cell with a nucleic acid molecule encoding Bcl-6, or encoding a homologue thereof, or a functional part or a functional derivative thereof. This way, it is possible to directly regulate the amount of Bcl-6 expression product in said B cell. Also provided is therefore a method according to the invention, wherein expression of Bcl-6 in said at least one B cell is induced, enhanced and/or maintained by providing said B cell with a nucleic acid molecule encoding Bcl-6, or encoding a homologue, or a functional part, or a functional derivative of Bcl-6. In one embodiment, said nucleic acid molecule is constitutively active, meaning that Bcl-6, or a homologue, functional part or functional derivative thereof, is continuously expressed, independent of the presence of a regulator. In another embodiment, said nucleic acid molecule is inducible, meaning that the expression thereof is regulated by at least one inducer and/or repressor. This way, expression of said nucleic acid molecule is regulated at will. For instance, Tet-On and Tet-Off expression systems (for example Tet-On® and Tet-Off® Advanced Inducible Gene Expression Systems, Clontech) can be used for inducible expression of a nucleic acid sequence of interest. In these systems expression of the transcriptional activator (tTA) is regulated by the presence (Tet-On) or absence (Tet-Off) of tetracycline (TC) or a derivative like doxycycline (dox). In principle, tTA is composed of the *Escherichia coli* Tet repressor protein (TetR) and the Herpes simplex virus transactivating domain VP16, tTA regulates transcription of a nucleic acid sequence of interest under the control of a tetracycline-responsive element (TRE) comprising the Tet operator (TetO) DNA sequence and a promoter sequence, for instance the human cytomegalovirus (hCMV) promoter. A nucleic acid sequence encoding, for instance, Bcl6, or a homologue or functional part or functional derivative thereof, can be placed downstream of this promoter.

In the Tet-off system, tTA binds to TRE in the absence of TC or dox and transcription of a nucleic acid sequence of interest is activated, whereas in the presence of TC or dox tTA cannot bind TRE and expression of a nucleic acid sequence of interest is inhibited. In contrast, the Tet-on system uses a reverse tTA (rtTA) that can only bind the TRE in the presence of dox. Transcription of a nucleic acid sequence of interest is inhibited in the absence of dox and activated in the presence of dox.

In another embodiment, inducible expression is executed using a hormone inducible gene expression system such as for instance an ecdysone inducible gene expression system (for example RheoSwitch®, New England Biolabs) (Christopherson, K. S. et al. PNAS 89, 6314-8 (1992)). Ecdysone is an insect steroid hormone from for example *Drosophila melanogaster*. In cells transfected with the ecdysone receptor, a heterodimer consisting of the ecdysone receptor (Ecr) and retinoid X receptor (RXR) is formed in the presence of an ecdyson agonist selected from ecdysone, one of its analogues such as muristerone A and ponasterone A, and a non-steroid ecdysone agonist. In the presence of an agonist. Ecr and RXR interact and bind to an ecdysone response element that is present on an expression cassette. Expression of a nucleic acid sequence of interest that is placed in an expression cassette downstream of the ecdysone response element is thus induced by exposing a B-cell to an ecdyson agonist.

In yet another embodiment of the invention inducible expression is executed using an arabinose-inducible gene expression system (for example pBAD/gIII kit, Invitrogen) (Guzman, L. M. et al. Bacteriol 177, 4121-4130 (1995)). Arabinose is a monosaccharide containing five carbon atoms. In cells transfected with the arabinose-inducible promoter PBAD, expression of a nucleic acid sequence of interest placed downstream of PBAD can then be induced in the presence of arabinose.

It is also possible to use (a nucleic acid molecule encoding) a Bcl-6 protein, or a homologue or functional part or functional derivative thereof, wherein the activity of said Bcl-6 or homologue or functional part or functional derivative is regulated by at least one inducer and/or repressor. A non-limiting example is a fusion protein wherein a regulatory element is fused to a sequence encoding at least part of Bcl-6. For instance, an estrogen receptor (ER) is fused to Bcl-6, resulting in fusion protein ER-Bcl-6. This fusion protein is inactive because it forms a complex with heat shock proteins in the cytosol. Upon administration of the exogenous inducer 4 hydroxy-tamoxifen (4HT), the fusion protein ER-Bcl-6 dissociates from the heat shock proteins, so that the Bcl-6 part of the fusion protein becomes active.

As used herein, the term "anti-apoptotic nucleic acid molecule" refers to a nucleic acid molecule, which is capable of delaying and/or preventing apoptosis in a B cell. Preferably, said anti-apoptotic nucleic acid molecule is capable of delaying and/or preventing apoptosis in a plasmablast-like B cell, which is typically present in a B cell culture as used in the invention. Preferably, an anti-apoptotic nucleic acid molecule is used which comprises an exogenous nucleic acid molecule. This means that either a nucleic acid sequence is used which is not naturally expressed in B cells, or that an additional copy of a naturally occurring nucleic acid sequence is used, so that expression in the resulting B cells is enhanced as compared to natural B cells in vivo. Various anti-apoptotic nucleic acid molecules are known in the art, so that various embodiments are available. Preferably, an anti-apoptotic nucleic acid molecule is used which is an anti-apoptotic member of the Bcl-2 family because anti-apoptotic Bcl-2 proteins are good apoptosis inhibitors in B cells. Many processes that are controlled by the Bcl-2 family (which family includes both pro- and anti-apoptotic proteins) relate to the mitochondrial pathway of apoptosis. The use of anti-apoptotic Bcl-2 family members Bcl-2, Bcl-xL, Bcl-w, Bcl-2-related protein A1 (also named Bcl2-A1 or A1), Bcl-2 like 10 (Bcl2L10) and Mcl-1, or a homologue thereof, or a functional part or functional derivative thereof, is preferred because Bcl-2, Bcl-xL, Bcl-w, A1, Bcl2L10 and Mcl-1 are generally integrated with the outer mitochondrial membrane. They directly bind and inhibit the pro-apoptotic proteins that belong to the Bcl-2 family to protect mitochondrial membrane integrity.

A preferred embodiment therefore provides a method according to the invention, wherein said anti-apoptotic nucleic acid molecule comprises an anti-apoptotic gene of the Bcl2 family, preferably Bcl-xL or Mcl-1 or Bcl-2 or A1 or Bcl-w or Bcl2L10, or a homologue thereof, or a functional part or a functional derivative thereof.

In one embodiment, expression of Bcl-xL or Mcl-1 or Bcl-2 or A1 or Bcl-w or Bcl210, or a homologue thereof, is induced, enhanced or maintained by administering at least one compound, capable of promoting expression of any of these anti-apoptotic genes, to B cell(s), or by culturing B cells in the presence of such compound(s). Further provided is therefore a method according to the invention, comprising:

providing said B cell with a compound capable of directly or indirectly enhancing expression of Bcl-xL and/or Mcl-1 and/or Bcl-2 and/or A1 and/or Bcl-w and/or Bcl210, or a homologue thereof; and/or culturing said B cell in the presence of a compound capable of directly or indirectly enhancing expression of Bcl-xL and/or Mcl-1 and/or Bcl-2 and/or A1 and/or Bcl-w and/or Bcl2L10, or a homologue thereof.

Preferably, however, a B cell is provided with at least one nucleic acid molecule encoding an anti-apoptotic gene of the Bcl2 family, preferably selected from the group consisting of Bcl-xL, Mcl-1, Bcl-2, A1, Bcl-w, Bcl2L10, and homologues thereof and functional parts thereof and functional derivatives thereof.

This way, it is possible to directly enhance the amount of expression product in said B cell. Also provided is therefore a method according to the invention, comprising providing said B cell with at least one nucleic acid molecule encoding an anti-apoptotic gene of the Bcl2 family, preferably selected from the group consisting of Bcl-xL, Mcl-1, Bcl-2, A1, Bcl-w, Bcl2L10, and homologues thereof, and functional parts and functional derivatives thereof. In one embodiment, said nucleic acid molecule is constitutively active, meaning that said nucleic acid molecule is continuously expressed. In another embodiment, said nucleic acid molecule is inducible, meaning that the expression thereof is regulated by at least one inducer and/or repressor. Non-limiting examples of inducible nucleic acid expression systems known in the art are described herein before.

In a particularly preferred embodiment said anti-apoptotic nucleic acid molecule encodes Bcl-xL or Mcl-1, or a homologue thereof, or a functional part or a functional derivative thereof. According to the present invention, a combination of Bcl-6 and Bcl-xL is particularly well capable of increasing the replicative life span of B-cells, thereby forming long term cultures of the resulting plasmablast-like B-cells. The same holds true for a combination of Bcl-6 and Mcl-1. Most preferably, said anti-apoptotic nucleic acid encodes Bcl-xL or a functional part or a functional derivative thereof.

A functional part of Bcl-6, Bcl-xL, Mcl-1, Bcl-2, A1, Bcl-w or Bcl2L10, or of a homologue thereof, is a proteinaceous molecule that has the same capability—in kind, not necessarily in amount—of increasing the replicative life span of a B cell as compared to natural Bcl-6, Bcl-xL, Mcl-1, Bcl-2, A1, Bcl-w or Bcl2L10, or a homologue thereof, respectively. Such functional part is for instance devoid of amino acids that are not, or only very little, involved in said capability.

For instance, functional parts of Bcl-xL. Mcl-1, Bcl-2, A1, Bcl-w and Bcl2L10, or of a homologue thereof, are defined herein as fragments of Bcl-xL, Mcl-1, Bcl-2, A1, Bcl-w and Bcl2L10, respectively, or of a homologue thereof, which have retained the same kind of anti-apoptotic characteristics as full length Bcl-xL, Mcl-1, Bcl-2, A1, Bcl-w and Bcl2L10, respectively, or a homologue thereof (in kind, but not necessarily in amount). Functional parts of Bcl-xL, Mcl-1, Bcl-2, A1, Bcl-w or Bcl2L10, or of a homologue thereof, are typically shorter fragments of Bcl-xL. Mcl-1, Bcl-2, A1, Bcl-w or Bcl2L10, respectively, or of a homologue thereof, which are capable of delaying and/or preventing apoptosis in a B-cell. Such functional parts are for instance devoid of sequences which do not significantly contribute to the anti-apoptotic activity of Bcl-xL. Mcl-1, Bcl-2, A1, Bcl-w and Bcl2L10. A functional part of Bcl-6, or of a homologue thereof, is typically a shorter fragment of Bcl-6, or a shorter fragment of a homologue thereof, which is also capable of increasing the replicative life span of a B cell.

A functional derivative of Bcl-6, Bcl-xL, Mcl-1, Bcl-2, A1, Bcl-w or Bcl2L10, or of a homologue thereof, is defined as a Bcl-6, Bcl-xL. Mcl-1, Bcl-2, A1, Bcl-w or Bcl2L10 protein, respectively, or a homologue thereof, which has been altered but has maintained its capability (in kind, not necessarily in amount) of increasing the replicative life span of a B cell. A functional derivative is provided in many ways, for instance through conservative amino acid substitution wherein one amino acid is substituted by another amino acid with generally similar properties (size, hydrophobicity, etc), such that the overall functioning is not seriously affected. Alternatively, a functional derivative for instance comprises a fusion protein with a detectable label or with an inducible compound.

Besides increasing Bcl-6 expression and the expression of an anti-apoptotic nucleic acid molecule, it is also advantageous to induce, enhance and/or maintain expression of Blimp-1, or a homologue thereof, in a B-cell. One aspect thus provides a method according to the invention, wherein the method further comprises inducing, enhancing and/or maintaining expression of Blimp-1, or a homologue thereof, in said at least one B-cell.

The extent of expression of Blimp-1, or of a homologue thereof, in a B cell is regulated in a variety of ways. In one embodiment, a B cell is provided with a compound, which is capable of directly or indirectly increasing expression of Blimp-1, or of a homologue thereof. Additionally, or alternatively, a B cell is cultured in the presence of a compound capable of directly or indirectly increasing expression of Blimp-1, or of a homologue thereof. Further provided is therefore a method according to the invention, further comprising:

providing said B cell with a compound capable of directly or indirectly increasing expression of Blimp-1, or expression of a Blimp-1 homologue; and/or culturing said B cell in the presence of a compound capable of directly or indirectly increasing expression of Blimp-1, or expression of a Blimp-1 homologue.

Said compound capable of increasing Blimp-1 expression most preferably comprises IL21. Hence, in one preferred embodiment of the present invention, B cells are cultured in the presence of IL21, at least during part of the culture time.

In another embodiment said compound capable of increasing Blimp-expression comprises a Signal Transducer of Activation and Transcription 3 (STAT3) protein or a functional part or a functional derivative thereof, and/or a nucleic acid molecule coding therefore. STAT3 is a signal transducer, which is involved in B cell development and differentiation. STAT3 is capable of upregulating Blimp-1 expression. In one preferred embodiment, a B cell is provided with a nucleic acid molecule encoding STAT3 or a functional part or a functional derivative thereof, wherein the expression of said nucleic acid molecule is regulated by an exogenous inducer of repressor, so that the extent of STAT3 expression is regulated at will. For instance, one of the earlier mentioned inducible expression systems is used. In one embodiment a fusion product comprising STAT3, or a functional part or a functional derivative, and ER is used. For instance, a B cell is provided with a nucleic acid molecule encoding an estrogen receptor (ER) and STAT3 as a fusion protein ER-STAT3. This fusion protein is inactive because it forms a complex with heat shock proteins in the cytosol. This way, STAT3 is unable to reach the nucleus and Blimp-1 expression is not enhanced. Upon administration of the exogenous inducer 4 hydroxy-tamoxifen (4HT), the fusion protein ER-STAT3 dissociates from the heat shock proteins, so that STAT3 is capable of entering the nucleus and activating Blimp-1 expression.

As used herein, a functional part of STAT3 is defined as a fragment of STAT3 that has the same capability—in kind, not necessarily in amount—of increasing expression of Blimp-1, or of a homologue thereof, as compared to natural STAT3. Such functional part is for instance devoid of amino acids that are not, or only very little, involved in said capability.

A functional derivative of STAT3 is defined as a STAT3 protein, which has been altered but has maintained its capability (in kind, not necessarily in amount) of increasing expression of Blimp-1, or of a homologue thereof. A functional derivative is provided in many ways, for instance through conservative amino acid substitution wherein one amino acid is substituted by another amino acid with generally similar properties (size, hydrophobicity, etc), such that the overall functioning is not seriously affected. Alternatively, a functional derivative for instance comprises a fusion protein with a detectable label or with an inducible compound.

Since STAT3 is capable of increasing expression of Blimp-1, it is also possible to indirectly increase expression of Blimp-1, or of a Blimp-1 homologue, by administering a compound capable of increasing the activity and/or expression of STAT3. In one embodiment, a B cell is therefore provided with a compound that is capable of enhancing the activity of STAT3, so that expression of Blimp-1, or of a Blimp-1 homologue, is indirectly enhanced.

STAT3 is activated in a variety of ways. Preferably, STAT3 is activated by providing a B cell with a cytokine. Cytokines, being naturally involved in B cell differentiation, are very effective in regulating STAT proteins. Very effective activators of STAT3 are IL21 and IL6, but also IL2, IL7, IL10, IL15 and IL27 are known to activate STAT3. Moreover, Toll-like receptors (TLRs), which are involved in innate immunity, are also capable of activating STAT3. One embodiment therefore provides a method of the invention, wherein said B cell is cultured in the presence of IL21, IL2, IL6, IL7, IL10, IL15 and/or IL27. Most preferably IL21 is used, since IL21 is particularly suitable for upregulating Blimp-1 expression, even when Blimp-1 expression is counteracted by BCL6.

Additionally, or alternatively a mutated Janus kinase (JAK), or a mutated homologue of a JAK, is used in order to activate STAT3. Naturally, a JAK is capable of phosphorylating STAT3 after it has itself been activated by at least one cytokine. A mutated Janus kinase, or a mutated homologue of a JAK, capable of activating STAT3 independently of the presence of cytokines, is particularly suitable in a method according to the present invention.

In yet another embodiment, expression of Blimp-1, or of a Blimp-1 homologue, is increased by providing a B cell with a suppressor of cytokine signalling (SOCS) protein, or a SOCS homologue, and/or by activating a SOCS protein or a SOCS homologue within said cell. Alternatively, or additionally, at least one of the E-proteins E47, E12, E2-2 and HEB is used in order to increase expression of Blimp-1, or expression of a Blimp-1 homologue. E47 is a transcription factor that belongs to a family of helix-loop-helix proteins, named E-proteins. There are four E-proteins, E12, E47, E2-2 and HEB, which are involved in lymphocyte development. E12 and E47 are encoded by one gene, named E2A, which is spliced differently. E proteins have been described as tumor suppressors. One of the specific targets of E47 are the Socs1 and Socs3 genes.

One aspect thus provides a method according to the present invention, further increasing expression of Blimp-1 in a B cell by providing said B cell with a compound capable of directly or indirectly increasing expression of Blimp-1 and/or culturing said B cell in the presence of a compound capable of directly or indirectly increasing expression of Blimp-1, wherein said compound comprises:

STAT3 or a functional part or a functional derivative thereof, and/or a compound capable of activating STAT3, and/or a compound capable of enhancing expression of STAT3, and/or IL21, IL2, IL6, IL7, IL10, IL15, IL27, a SOCS protein, one of the E-proteins E47, E12, E2-2 or HEB, a mutated Janus kinase and/or a nucleic acid sequence encoding STAT3, or a homologue or a functional part or a functional derivative thereof.

Most preferably, said compound is IL21.

As described above, methods according to the present invention are particularly suitable for developing medicaments and vaccines, preferably against tumors, pathogens and/or autoimmune diseases. One aspect therefore provides a method according to the invention, further comprising preparing a medicament comprising T cells that recognize at least one T cell epitope of or encoded by the tested compounds. Further provided is also a medicament comprising T cells that recognize a disease-specific epitope, preferably a tumor-specific epitope or a T cell epitope from a pathogen or an autoantigen, when obtained with a method according to the invention. Said medicament preferably further comprises a pharmaceutically acceptable carrier, diluent or excipient. Said medicament is preferably a medicament against melanoma, epithelial cancer, lung squamous cell carcinoma, lung adenocarcinoma, stomach cancer, esophagus cancer, lung small cell carcinoma, colorectal cancer, bladder cancer, uterine cancer, cervical cancer, liver cancer, head and neck cancer, kidney clear cell cancer, B cell lymphoma, kidney papillary cancer, breast cancer, pancreas cancer, myeloma, ovary cancer, prostate cancer, glioblastoma, glioma, neuroblastoma, medulloblastoma, CLL, chromophobe renal cell carcinoma, thyroid cancer, ALL, AML or pilocytic astrcytoma. Most preferably, said medicament is against melanoma or epithelial cancer.

In some embodiments, said medicament is against an infectious disease, preferably caused by a virus, bacterium or parasite.

As used herein, the term "medicament against" a certain disease means that said medicament is capable of at least in part treating or preventing, or delaying, the onset or progression of said disease. Additionally, or alternatively, said medicament is capable of at least in part alleviating at least one symptom of said disease.

Another aspect provides a method according to the invention, further comprising identifying at least one T cell epitope that is recognized by a T cell in the test assay. Such epitope recognized by a T cell is preferably used for preparing an immunogenic composition, or a prophylactic agent or vaccine.

A further aspect provides a method according to the invention, further comprising preparing an immunogenic composition, or a prophylactic agent or vaccine, comprising a B cell which displays at its surface at least one T cell epitope recognized by a T cell in the test assay. An immunogenic composition, or a prophylactic agent or vaccine, according to the invention preferably further comprises a pharmaceutically acceptable carrier, diluent or excipient.

An immunogenic composition, or a prophylactic agent or vaccine, comprising a disease-specific T cell epitope, preferably a tumor-specific T cell epitope or a T cell epitope from a pathogen or an autoantigen, when obtained with a method according to the invention, is also provided. Said T cell epitope may be displayed on the surface of an antigen-presenting cell, preferably a B cell as used herein.

As discussed before, one of the advantages of a method according to the present invention is the very low extent (if any) of background signals that is obtained, so that even a low extent of T cell recognition can be detected. This is particularly advantageous if the B cells, loaded with test compounds, are incubated with T cells from an individual suffering from a disorder. If disease-specific T cell levels within said individual are low, epitope recognition by these low amounts of T cells is easily overlooked in existing EBV immortalized B cell assays due to many background signals caused by the relatively high frequencies of EBV-specific T cells in most individuals. A method according to the invention provides a solution for this. As shown in the Examples, even low numbers of T cell epitope recognizing T cells are detectable with a method according to the invention. For instance, with the use of EBV immortalized B cells as APCs only one very prominent disease-specific T cell response was detected, wherein the amount of the T cells of interest was as large as 24% of the total T cells within the infusion cell product. On the other hand, with the use of a method according to the present invention, using B cells wherein the expression of Bcl-6 and Bcl-xL is induced, enhanced and/or maintained, it has become possible to detect T cell responses with a much lower frequency, even as low as 0.264-0.053% (FIGS. 3b and 3c). One preferred embodiment therefore provides a method according to the invention, wherein said T cells are from a sample from said individual, characterized in that the proportion of T cells specific for a T cell epitope that is associated with said disease, relative to the total amount of T cells, is lower than 24%, more preferably lower than 23%, more preferably lower than 22%, more preferably lower than 21%, more preferably lower than 20%, more preferably lower than 15%, more preferably lower than 10%, more preferably lower than 9%, more preferably lower than 8%, more preferably lower than 7%, more preferably lower than 6%, more preferably lower than 5% in said sample or in a T cell culture after in vitro expansion of said sample.

In preferred embodiments, a method according to the invention is provided wherein said T cells are from a sample from said individual, characterized in that the proportion of T cells specific for a T cell epitope that is associated with a disorder of interest, relative to the total amount of T cells, is lower than 1.9%, more preferably lower than 1.8%, more preferably lower than 1.7%, more preferably lower than 1.6%, more preferably lower than 1.5% in said sample or in a T cell culture after in vitro expansion of said sample.

In further preferred embodiments, said T cells are from a sample from said individual, characterized in that the proportion of T cells specific for a T cell epitope that is associated with a disorder of interest, relative to the total amount of T cells, is lower than 1.0%, more preferably lower than 0.9%, more preferably lower than 0.8%, more preferably lower than 0.7%, more preferably lower than 0.6%, more preferably lower than 0.5%, more preferably lower than 0.4%, more preferably lower than 0.3% in said sample or in a T cell culture after in vitro expansion of said sample. In one embodiment, said proportion is between 0.264% and 0.053%. In further embodiments, said proportion is 0.264% or lower. In further embodiments, said proportion is 0.246% or lower. In further embodiments, said proportion is 0.096% or lower. In further embodiments, said proportion is 0.053% or lower.

Also provided is a method according to the invention, wherein a sample from said individual is used, or wherein T cells of a resulting T cell culture after in vitro expansion of said sample are used, wherein the percentage of T cells specific for a T cell epitope that is associated with said disease, relative to the total number of T cells in said sample or in said resulting in vitro T cell culture, is lower than 24%, more preferably lower than 23%, more preferably lower than 22%, more preferably lower than 21%, more preferably lower than 20%, more preferably lower than 15%, more preferably lower than 10%, more preferably lower than 9%, more preferably lower than 8%, more preferably lower than 7%, more preferably lower than 6%, more preferably lower than 5%.

In preferred embodiments, a method according to the invention is provided wherein a sample from said individual is used, or wherein T cells of a resulting T cell culture after in vitro expansion of said sample are used, wherein the percentage of T cells specific for a T cell epitope that is associated with a disorder of interest, relative to the total number of T cells in said sample or in said resulting in vitro T cell culture, is lower than 1.9%, more preferably lower than 1.8%, more preferably lower than 1.7%, more preferably lower than 1.6%, more preferably lower than 1.5%.

In further preferred embodiments, a method according to the invention is provided wherein a sample from said individual is used, or wherein T cells of a resulting T cell culture after in vitro expansion of said sample are used, wherein the percentage of T cells specific for a T cell epitope that is associated with a disorder of interest, relative to the total number of T cells in said sample or in said resulting in vitro T cell culture, is lower than 1.0%, more preferably lower than 0.9%, more preferably lower than 0.8%, more preferably lower than 0.7%, more preferably lower than 0.6%, more preferably lower than 0.5%, more preferably lower than 0.4%, more preferably lower than 0.3%. In one embodiment, said percentage is between 0.264% and 0.053%. In further embodiments, said percentage is 0.264% or lower. In further embodiments, said percentage is 0.246% or lower. In further embodiments, said percentage is 0.096% or lower. In further embodiments, said percentage is 0.053% or lower.

Said disease or said disorder is preferably selected from the group consisting of:
cancer, preferably melanoma or epithelial cancer, and
an infectious disease, preferably a viral infection, a bacterial infection or a parasite infection, and
an autoimmune disease, preferably multiple sclerosis, diabetes or coeliac disease.

In one preferred embodiment, said T cells are CD4+ T cells. One preferred aspect therefore provides a method according to the invention, wherein said T cells are CD4+ T cells from a sample from an individual who is suffering from, or who has suffered from, a disease, characterized in that the concentration in said sample, or in a T cell culture after in vitro expansion of said sample, of CD4+ T cells that are specific for a T cell epitope that is associated with said disease is lower than 24% of the total amount of CD4+ T cells in said sample or in said T cell culture. The proportion of certain CD4+ T cells of interest, compared to the total amount of CD4+ T cells in a sample or T cell culture, is called the frequency. Preferably, the frequency of CD4+ T cells that are specific for a T cell epitope that is associated with said disease is lower than 23%, more preferably lower than 22%, more preferably lower than 21%, more preferably lower than 20%, more preferably lower than 15%, more preferably lower than 10%, more preferably lower than 9%, more preferably lower than 8%, more preferably lower than 7%, more preferably lower than 6%, and even more preferably lower than 5% of the total amount of CD4+ T cells in said sample or in said T cell culture. In one embodiment, the frequency of CD4+ T cells that are specific for a T cell epitope that is associated with said disease is between 1.7% and 4.5% of the total CD4+ cells in said sample or in said T cell culture.

In preferred embodiments, a method according to the invention is provided wherein said T cells are CD4+ T cells from a sample from an individual who is suffering from, or who has suffered from, a disease, characterized in that the concentration in said sample, or in a T cell culture after in vitro expansion of said sample, of CD4+ T cells that are specific for a T cell epitope that is associated with said disease is lower than 1.9%, more preferably lower than 1.8%, more preferably lower than 1.7%, more preferably lower than 1.6%, more preferably lower than 1.5% of the total amount of CD4+ T cells in said sample or in said T cell culture.

In further preferred embodiments, a method according to the invention is provided wherein said T cells are CD4+ T cells from a sample from an individual who is suffering from, or who has suffered from, a disease, characterized in that the concentration in said sample, or in a T cell culture after in vitro expansion of said sample, of CD4+ T cells that are specific for a T cell epitope that is associated with said disease is lower than 1.0%, more preferably lower than 0.9%, more preferably lower than 0.8%, more preferably lower than 0.7%, more preferably lower than 0.6%, more preferably lower than 0.5%, more preferably lower than 0.4%, more preferably lower than 0.3% of the total amount of CD4+ T cells in said sample or in said T cell culture. In one embodiment, said CD4+ T cell concentration is between 0.264% and 0.053%. In further embodiments, said concentration is 0.264% or lower. In further embodiments, said concentration is 0.246% or lower. In further embodiments, said concentration is 0.096% or lower. In further embodiments, said concentration is 0.053% or lower.

Said T cell epitope that is associated with said disease is preferably a tumor-specific T cell epitope or a T cell epitope from a pathogen or a T cell epitope from an autoantigen.

Also low levels of CD8+ T cells are detectable with a method according to the invention. One preferred aspect therefore provides a method according to the invention, wherein said T cells are CD8+ T cells from a sample from an individual who is suffering from, or who has suffered from, a disease, characterized in that the proportion in said sample, or in a T cell culture after in vitro expansion of said sample, of CD8+ T cells that are specific for a T cell epitope that is associated with said disease is lower than 24% of the total amount of CD8+ T cells in said sample or in said T cell culture. Preferably, the frequency of CD8+ T cells that are specific for a T cell epitope that is associated with said disease, relative to the total amount of CD8+ T cells in said sample or in said T cell culture, is lower than 23%, more preferably lower than 22%, more preferably lower than 21%, more preferably lower than 20%, more preferably lower than 15%, more preferably lower than 10%, more preferably lower than 9%, more preferably lower than 8%, more preferably lower than 7%, more preferably lower than 6%, and even more preferably lower than 5% of the total amount of CD8+ T cells in said sample or in said T cell culture.

In preferred embodiments, a method according to the invention is provided wherein said T cells are CD8+ T cells from a sample from an individual who is suffering from, or who has suffered from, a disease, characterized in that the proportion in said sample, or in a T cell culture after in vitro expansion of said sample, of CD8+ T cells that are specific for a T cell epitope that is associated with said disease is lower than 1.9%, more preferably lower than 1.8%, more preferably lower than 1.7%, more preferably lower than 1.6%, more preferably lower than 1.5% of the total amount of CD8+ T cells in said sample or in said T cell culture.

In further preferred embodiments, a method according to the invention is provided wherein said T cells are CD8+ T cells from a sample from an individual who is suffering from, or who has suffered from, a disease, characterized in that the proportion in said sample, or in a T cell culture after in vitro expansion of said sample, of CD8+ T cells that are specific for a T cell epitope that, is associated with said disease is lower than 1.0%, more preferably lower than 0.9%, more preferably lower than 0.8%, more preferably lower than 0.7%, more preferably lower than 0.6%, more preferably lower than 0.5%, more preferably lower than 0.4%, more preferably lower than 0.3% of the total amount of CD8+ T cells in said sample or in said T cell culture. As described hereinbefore, said T cell epitope that is associated with said disease is preferably a tumor-specific T cell epitope or a T cell epitope from a pathogen or a T cell epitope from an autoantigen.

Also provided is a method according to the invention, wherein a sample from an individual suffering from, or having suffered from, a disorder is used, or wherein T cells of a resulting T cell culture after in vitro expansion of said sample are used, wherein the proportion of T cells specific for a T cell epitope that is associated with said disease, preferably for a tumor-specific T cell epitope or a T cell epitope from a pathogen or a T cell epitope from an autoantigen, relative to the total number of T cells in said sample or in said resulting in vitro T cell culture, is lower than 24%, more preferably lower than 23%, more preferably lower than 22%, more preferably lower than 21%, more preferably lower than 20%, more preferably lower than 15%, more preferably lower than 10%, more preferably lower than 9%, more preferably lower than 8%, more preferably lower than 7%, more preferably lower than 6%, and even more preferably lower than 5% of the total amount of T cells in said sample or in said resulting T cell culture. In some embodiments, said proportion in said sample or in said resulting in vitro T cell culture of T cells that are specific for a T cell epitope that is associated with said disease, relative to the total number of T cells in said sample or in said resulting in vitro T cell culture, is between 1.7% and 4.5%, preferably lower than 1.9%, more preferably lower than 1.8%, more preferably lower than 1.7%, more preferably lower than 1.6%, more preferably lower than 1.5%, more preferably lower than 1.0%, more preferably lower than 0.9%, more preferably lower than 0.8%, more preferably lower than 0.7%, more preferably lower than 0.6%, more preferably lower than 0.5%, more preferably lower than 0.4%, more preferably lower than 0.3% of the total amount of T cells in said sample or in said in vitro T cell culture. In one preferred embodiment, said T cells are CD4+ T cells.

Another aspect of the invention provides a use of a B cell for presenting an epitope of interest, characterized in that the in vitro replicative life span of said B cell is prolonged by inducing, enhancing and/or maintaining expression of Bcl-6 and/or STAT5 in said B cell and by inducing, enhancing and/or maintaining expression of an anti-apoptotic nucleic acid in said B cell. Said epitope is preferably a T cell epitope.

In one embodiment, a method according to the invention is used for testing the affinity of a B cell for a certain (test) compound. In this embodiment, B cells are incubated with large compounds such as for instance proteins or polypeptides that cannot be bound directly to the MHC molecules at the surface of the B cells. Instead, the compounds may, or may not, be internalized via the B cell receptor (BCR). If internalized, the compounds are processed and subsequently displayed at the surface of the B cell. Then the B cells are incubated with T cells. If a T cell appears to recognize a surface-bound peptide derived from a compound that was used in the assay, it is concluded that the B cells were capable of efficiently internalizing said compound. Hence, this way it is determined whether or not the B cells have a high affinity for one or more test compounds. A B cell with an affinity for one or more test compounds can then be selected for further use. In some embodiments, the affinities of several B cells for a given test compound are compared with each other. This is for instance possible using serial dilution experiments, wherein it is determined whether T cell activation still occurs when the B cells are incubated with decreasing concentrations of a given test compound. Subsequently, a B cell with a higher affinity for a test compound, as compared to the affinity of one or more other B cell(s) for said test compound, is preferably selected.

In a further embodiment, a method according to the invention is provided wherein compounds are used that comprise both at least one B cell epitope and at least one T cell epitope. Incubation of B cells with such compound results in efficient internalization and presentation of compound-derived peptides, and the resulting B cells will also be capable of eliciting a particularly high T cell response.

The invention is further explained in the following examples. These examples do not limit the scope of the invention, but merely serve to clarify the invention.

INCORPORATION OF SEQUENCE LISTING

Incorporated herein by reference in its entirety is an initial Sequence Listing for the herein application. The Sequence Listing is disclosed in a computer-readable ASCII text file titled, "seqlist_294_507_pct_us2541_3_PCT_US.txt", created on Apr. 28, 2020. The .txt file is 8.68 kb in size.

REFERENCES

Christopherson, K. S. et al. PNAS 89, 6314-8 (1992)
Davis et al. Nature Reviews Immunology. Vol. 11, 551-558 (2011)
Guzman. L. M. et al. Bacteriol 177, 4121-4130 (1995)
Rosenberg et al. Clin. Cancer. Res. 17, 4550-4557 (2011)
Schultze et al. J. Clin. Invest. Vol. 100. No. 11, 2757-2765 (1997)
Tran et al. Science 344, 641-645 (2014)

BRIEF DESCRIPTION OF THE DRAWINGS

FIG. 2. Characteristics of the mutational landscape in the analyzed melanoma lesions.

NKIRTIL018 and (b) NKIRTIL034. Dotted line indicates cytokine concentrations after co-culture of CD4+ T cells with unloaded B-cells.

FIG. 6. Analysis of cross-reactivity of intratumoral CD4+ T cells against a non-autologous, mutated peptide library. IFN-γ concentration in culture supernatant after 48 h co-culture of in vitro expanded intratumoral CD4+ T cells obtained from (a) NKIRTIL018 and (b) NKIRTIL034 with autologous B-cells loaded with peptide libraries of the respective other subject. Dotted line indicates IFN-γ production of CD4+ T cells after co-culture with unloaded B-cells. Identified neo-epitopes of NKIRTIL018 and NKIRTIL034 were used as positive control samples.

Figure 7A:
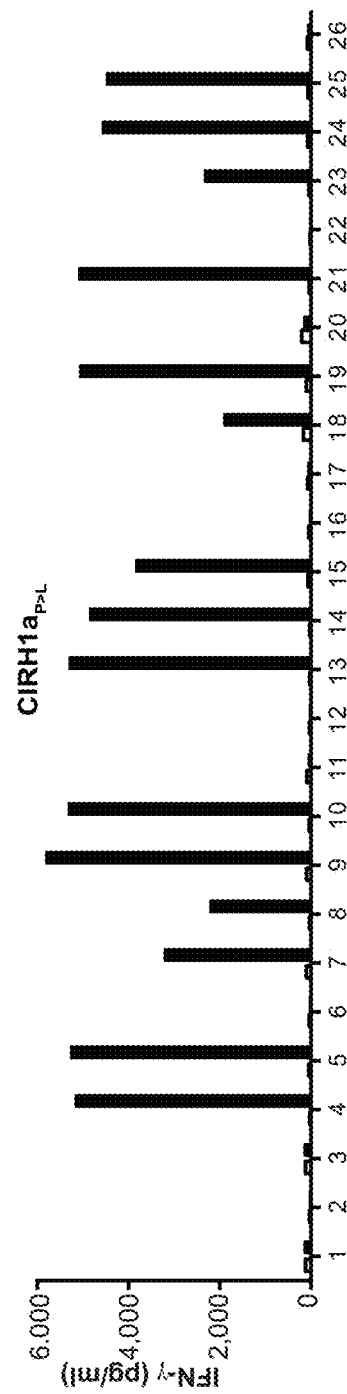
Figure 7B:
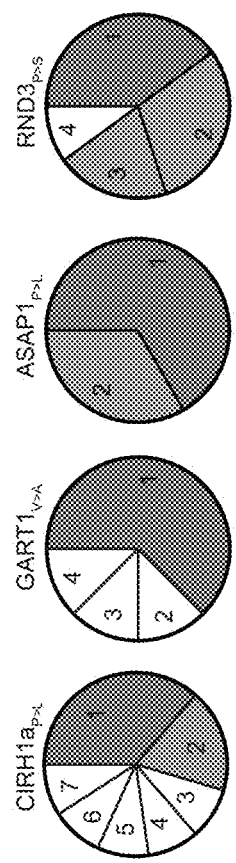
Figure 7D:
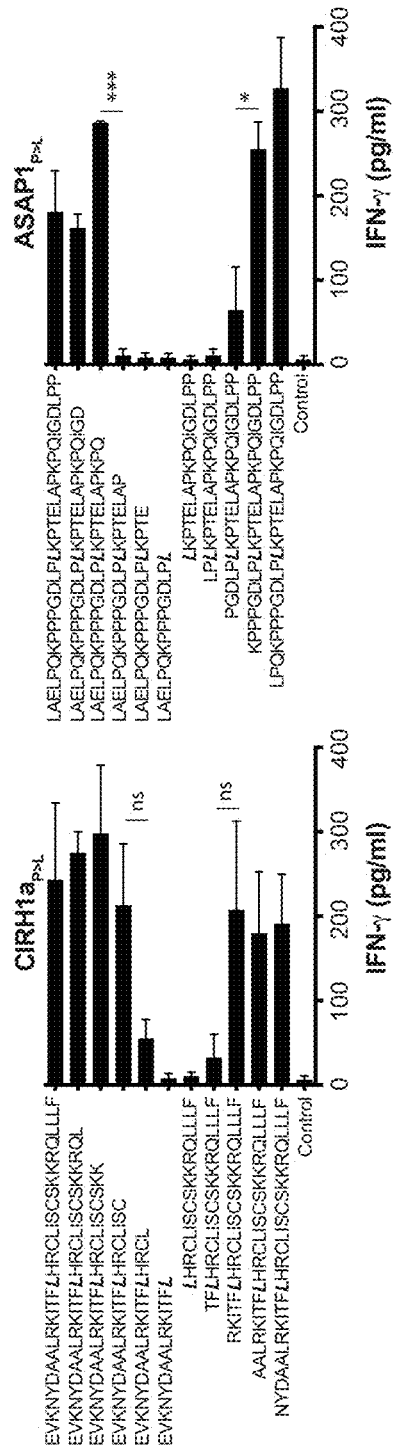

FIG. 7. Isolation and characterization of neo-epitope specific CD4+ T cells in human melanoma lesions. (a) IFN-γ concentration in culture supernatant after 48 h co-culture of CIRH1$_{P>L}$ reactive CD4+ T cell clones derived from NKIRTIL018 with unloaded (white bars) or peptide loaded (black bars) autologous B cells. (b) T cell receptor (TCR) repertoire diversity among neo-antigen reactive CD4+ T cell clones of NKIRTIL018 and NKIRTIL034. Numbers indicate different TCR clonotypes; grey segments indicate TCR clonotypes identified in at least two analyzed T cell clones. (c) IFN-γ concentration in culture supernatant after 48 h co-culture of neo-antigen reactive CD4+ T cell clones derived from NKIRTIL018 with autologous B-cells loaded with indicated concentrations of mutated peptide (open squares) or wildtype peptide (black circles). TCR clonotypes are indicated as determined in (b). (d) Mean IFN-γ concentration in culture supernatant after 48 h co-culture of neo-antigen reactive CD4-T cell clones derived from NKIRTIL018 with autologous B-cells loaded with truncated variants of the mutated peptide (n=2). Error bars depict s.d. CIRH1$_{P>L}$ P=0.1012 and P=0.1514, ASAP1$_{P>L}$ P=0.0005 and P=0.0474.

Figure 8:
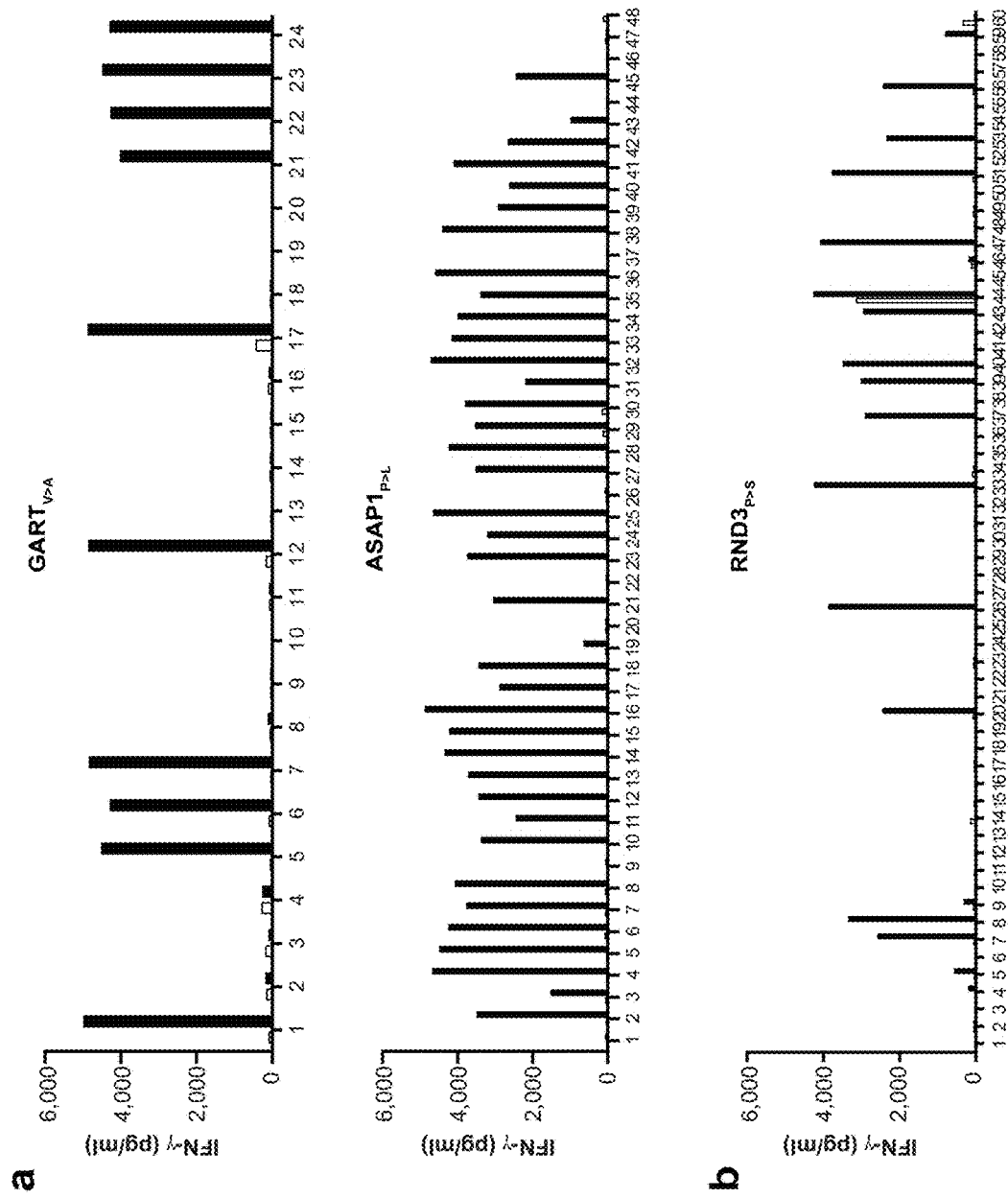

FIG. 8. Isolation of neo-epitope reactive CD4+ T cells from human melanoma lesions. IFN-γ concentration in culture supernatant after 48 h co-culture of (a) GART$_{V>A}$ and ASAP1$_{P>L}$ reactive CD4+ T cell clones derived from NKIRTIL018 and (b) RND3$_{P>S}$ reactive CD4+ T cell clones derived from NKIRTIL034 with unloaded (white bars) or peptide loaded (black bars) autologous B cells.

Figure 9:
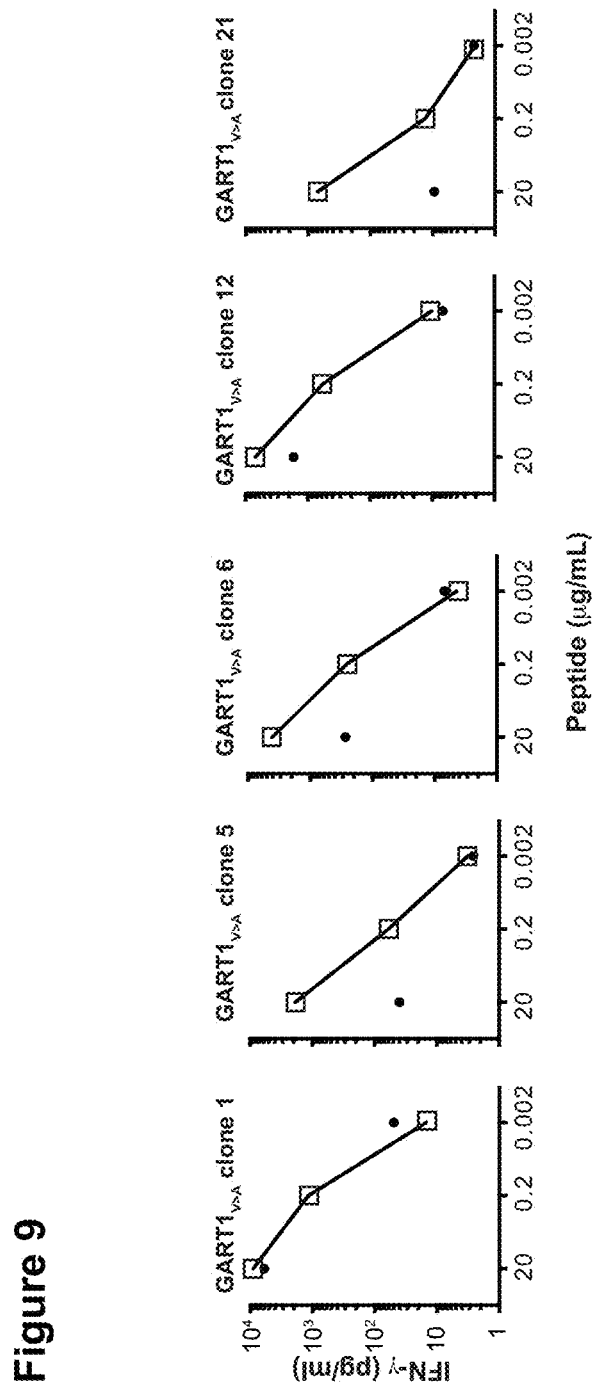

FIG. 9. Recognition of mutated and wildtype peptide by neo-antigen reactive T cell clones of NKIRTIL018. IFN-γ concentration in culture supernatant after 48 h co-culture of GART1$_{V>A}$ reactive CD4+ T cell clones derived from NKIRTIL018 with autologous B-cells loaded with indicated concentrations of mutated peptide (open squares) or wildtype peptide (black circles).

Figure 10:
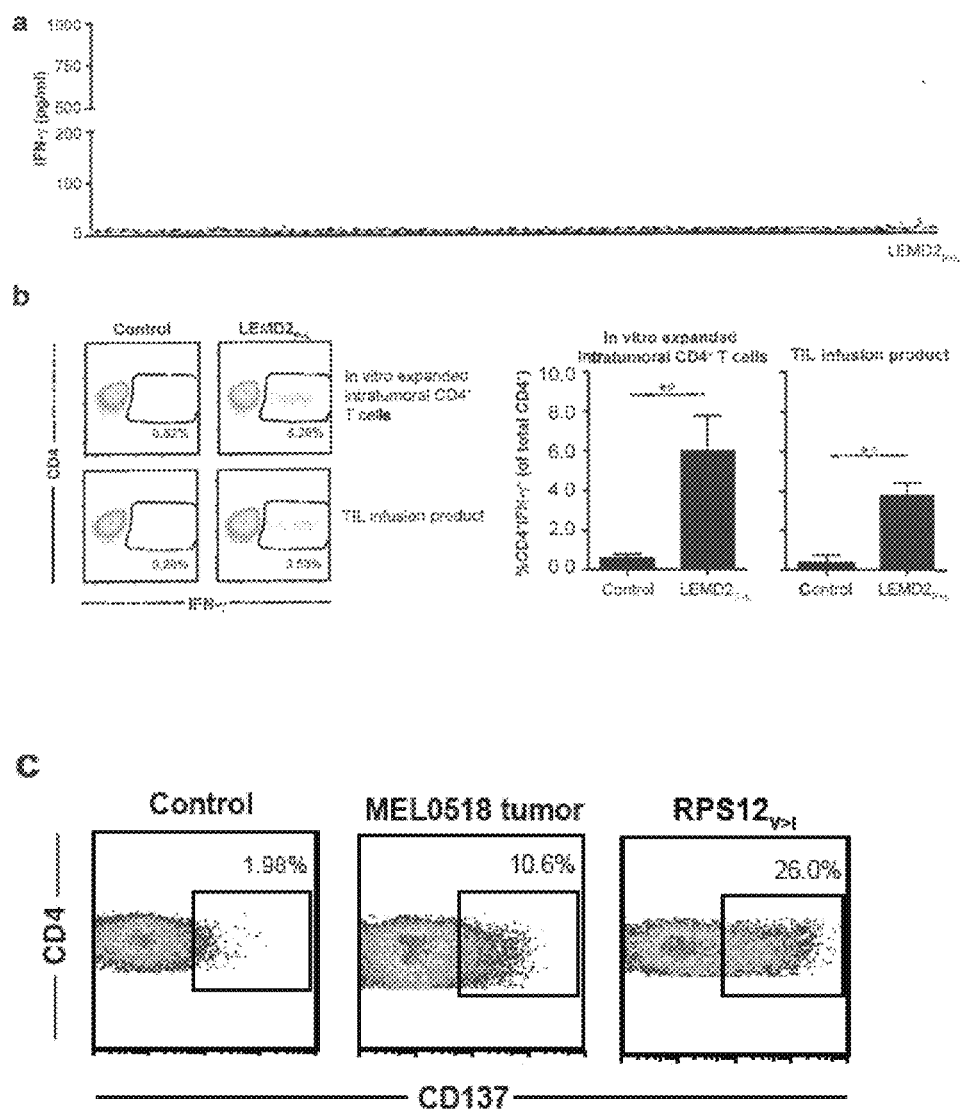

FIG. 10. Identification and enumeration of neo-antigen reactive CD4+ T cell products used for adoptive T cell therapy. (a) Mean IFNγ concentration in culture supernatant after a 48 h co-culture of peptide loaded, autologous B cells with in vitro expanded intratumoral CD4+ T cells. Dotted line indicates mean IFNγ production of CD4+ T cells after co-culture with unloaded B cells. (b) Detection of intracellular IFNγ levels after a 24 h co-culture of peptide loaded autologous B cells with either in vitro expanded intratumoral CD4+ T cells or with the TIL infusion product of NKIRTIL027. Flow cytometry plots depict single live CD4+ IFNγ+ T cells from a representative experiment. Bar graphs depict mean IFNγ concentrations over multiple experiments (n=3). P=0.0061 (in vitro expanded intratumoral CD4+ T cells) and 0.0011 (TIL infusion product). Error bars depict s.d. (c) Expression of CD 137 on CD4+ T cells within the T cell infusion product of subject BO after 16 h co-culture with autologous tumor cells or with RPS12$_{V>I}$ peptide loaded EBV immortalized B cells. Flow cytometry plots depict single, live. CD4+ T cells.

FIG. 11. Detection of neo-epitope specific CD8+ T cells in human melanoma lesion. (a) IFN-g concentration in culture supernatant after 48 h co-culture of 582 different 31-AA peptides loaded on autologous B-cells with in vitro expanded intratumoral CD8+ T cells (n=1). (b) IFN-g concentration in culture supernatant after 48 h co-culture of unloaded B cells, B cells loaded with an irrelevant epitope and B cells loaded with the TTC37$_{A>V}$ 31-AA peptide. (c) Percentage of CD8+ multimer+ T cells, after staining with HLA-A*01:01 multimers loaded with the TTC37 undecamer epitope.

EXAMPLES

Example 1

Intratumoral CD4+ T Cell Reactivity Against Mutated Antigens is Commonly Observed in Human Melanoma Methods Generation of TIL material, tumor cell lines and Bcl-6/Bcl-xL transduced B cells. PBMC and TIL material was obtained from individuals with stage IV melanoma in accordance with Dutch guidelines, when applicable following signed informed consent and after approval of the medical ethical committees at the NKI-AVL (Medisch Ethische Toetsingscommissie).

PBMC material was prepared by Ficoll-Isopaque density centrifugation. TIL material and short-term tumor lines were obtained from resected melanoma lesions. Fresh tumor material was minced and digested overnight in RPMI 1640 (Life Technologies) supplemented with penicillin-streptomycin (Roche), 0.01 mg ml$^{-1}$ pulmozyme (Roche) and 1 mg ml$^{-1}$ collagenase type IV (BD Biosciences). A tumor line was obtained by culture of the resulting cell suspension in RPMI 1640 supplemented with penicillin-streptomycin (Roche) and 10% (v/v) heat-inactivated Fetal Bovine Serum (Sigma-Aldrich). TIL were obtained by culturing the suspension cells in RPMI 1640 supplemented with penicillin-streptomycin, 10% (v/v) AB serum (Sanquin Blood Supply and Life Technologies), L-glutamine (Life Technologies) and 6000 IU ml$^{-1}$ rhIL-2 (Novartis).

Autologous B cells from PBMC material were immortalized as part of collaboration agreement by AIMM Therapeutics by Bcl-6/Bcl-xL gene transfer as previously described[15,16]. For a detailed description, see also WO 2007/067046. Bcl-6/Bcl-xL transduced B cells were cultured in IMDM (Life Technologies) supplemented by 10% (v/v) Fetal bovine serum (Hyclone), penicillin-streptomycin (Roche) and 50 ng ml$^{-1}$ rm-IL21 (AIMM Therapeutics) and stimulated every 3-5 days by irradiated (50 Gy) mouse L cell fibroblasts expressing CD40L (2:1 B cell-to/L cell ratio).

Exome sequencing. Genomic DNA was extracted from cell pellets using a DNeasy purification kit (Oiagen), fragmented using the Covaris S220 Focused-ultrasonicator (Woburn). DNA libraries were created using the Illumina TruSeq DNA library preparation kit. Exonic sequences were enriched capturing DNA fragments with the Sure Select Human All Exon 50 Mb Target Enrichment system (Agilent) 28, according to Agilent protocols with modifications. 1:2 of standard bait reaction was used and Block #3 in the hybridization mixture was replaced with a custom NKI-Block #3 to support the TruSeq DNA libraries in which the indexes require additional blocking. NKI-Block #3 consists of equal amounts of two DNA oligos (IDT-DNA) at 16.6 ug/ul:

NKI 3.1

(SEQ ID NO: 1)
5'AGATCGGAAGAGCACACGTCTGAACTCCAGTCACNNNNNNNATCTCGTA
TGCCGTCTTCTGCTTG/3'ddC/ 3'

NKI 3.2

(SEQ ID NO: 2)
5'CAAGCAGAAGACGGCATACGAGATNNNNNNNGTGACTGGAGTTCAGACG
TGTGCTCTTCCGATCT/3'ddC/ 3'

Captured library fragments were split into two fractions and both were PCR enriched (13 cycles) using the Illumina P5 and P7 oligonucleotides (IDT-DNA).

(SEQ ID NO: 3)
P5 primer: 5'AATGATAGGGCGACCACCGAGATCT 3', (SEQ ID NO: 4)
P7 primer: 5'CAAGCAGAAGACGGCATACGAG 3'.

Both PCR reactions quantified on a BioAnalyzer DNA7500 Chip (Agilent), equally combined and diluted to 10 nM concentrations for paired-end 75 bp sequencing on a Illumina HiSeq2000 sequencer. Reads were aligned to the human reference genome GRCh37 using BWA version 0.5.10[20]. PCR duplicates were filtered using Picard (http://picard.sourceforge.net) and realignment around insertions and deletions (indels) was performed using GATK toolkit[21].

Somatic single nucleotide variants (SNV) were called using Somatic-sniper[22] and filtered using a somatic score cut-off>34 and a minimum of 4 reads in both tumor and control. Somatic indels were called using the GATK somatic indel detector and filtered using a minimum variation frequency of 25% and having at least 5 reads showing the indel. Germ-line variants in the vicinity of detected somatic variants were identified using Samtools[23] and filtered using minimum coverage and minimum number of alternate reads of 10 and 6 reads, respectively. SNPeff[24] was then used to predict the effect of all variants on the Ensembl gene build version 65. Using a custom Perl script and the Ensembl API, coxling variants were edited into the cDNA sequence and subsequently translated into protein sequence. These protein sequences were separately generated for normal (only germline variants) and tumor samples (germline variants and tumor specific mutations).

RNA-sequencing. RNA was isolated using TriZol reagent (Life Technologies). Poly-A selected RNA libraries were prepared using the TruSeq RNA library protocol (Illumina) and Paired-end 50 bp sequencing was performed on an Illumina HiSeq2000. Reads were aligned to human reference genome GRCh37 using Tophat 1.4[25]. Expression values were calculated as FPKM using Cufflinks[26].

Peptide synthesis. Peptides were synthesized at the NKI Peptide synthesis facility (Amsterdam) using preloaded Wang resin with a SYRO II robot using standard Fmoc Solid Phase Peptide Chemistry, with PyBop and Dipea as activator and base.

Generation of CD4+ T cell material from TIL and detection of neo-antigen reactivity. Cell-sorting was performed on a FACSAria I (BD Biosciences) or MoFlo Astrios (Beckman Coulter). Bulk CD4+ T cell populations were generated from cryo-preserved TIL material by sorting of live single CD4+ T cells stained antibody against CD8 (BD Biosciences; SK1; 1:50) and CD4 (BD Biosciences; SK3; 1:50). Isolated live single CD4+ CD8− T cells were expanded using 30 ng ml$^{-1}$ CD3-specific antibody (OKT-3; Janssen-Cilag) and 3,000 IU ml$^{-1}$ rh-IL-2 (Novartis) in 1:1 (v/v) medium mixture of RPMI 1640 and AIM-V (Life Technologies) supplemented with 10% AB serum (Life Technologies). Glutamax (Life Technologies) at a 1:200 T cell/feeder cell ratio to obtain pure CD4+ T cell populations (routinely >97% CD4+) which were used for determination of T cell reactivity against neo-epitopes.

Detection of neo-epitope reactive CD4+ T cells. 1×10$^5$ Bcl-6/Bcl-xL transduced B cells per well were loaded with peptide (20 µg ml$^{-1}$ unless otherwise indicated) in 96-round-bottom plates for 18-24 hours in 200 µl IMDM medium (Life Technologies) supplemented by 10% (v/v) Fetal bovine serum (Hyclone), penicillin-streptomycin (Roche) and 50 ng ml$^{-1}$ rm-IL21 (AIMM Therapeutics). Afterwards, medium was removed and 1×10$^5$ CD4+ T cells were added per well in 200 µl RPMI 1640 (Life Technologies) supplemented by 10% (v/v) AB serum (Life Technologies), penicillin-streptomycin (Roche) and 50 ng ml$^{-1}$ rm-IL21 (AIMM Therapeutics). 48 hours later, culture supernatant was harvested and analyzed using Human $T_{H1}/T_{H2}/T_{H17}$ cytometric bead array (BD Biosciences) or IFN-γ Flex bead E7 cytometric bead array (BD Biosciences) according to manufacturer's guidelines. For detection of intracellular levels of IFN-γ by flow cytometry. CD4+ T cells were stimulated with peptide-loaded B cells for 24 hours. Subsequently, cells were stained using IR-Dye (Life Technologies) for exclusion of dead cells and the Cytofix/Cytoperm kit (BD Biosciences) and an antibody against IFN-γ (BD Biosciences; 25723; 1:50) according to the manufacturer's guidelines.

For isolation of live, IFN-γ producing CD4+ T cells. T cells were stimulated with peptide-loaded B cells for 6 hours. Subsequently, cells were stained using the IFN-γ secretion capture kit (Miltenyi Biotec) and an antibody for CD4 (BD Biosciences; SK3; 1:50). Single, live IFN-γ producing CD4+ T cells were sorted by flow cytometry and collected in 96-well round-bottom culture plates containing 2×10$^5$ irradiated PBMCs, 30 ng ml$^{-1}$ CD3-specific antibody (OKT-3; Janssen-Cilag) and 3.000 IU ml$^{-1}$ recombinant human IL-2 (Novartis) in 200 µl 1:1 (v/v) medium mixture of RPMI 1640 and AIM-V (Life Technologies) supplemented with 10% AB serum (Life Technologies), penicillin-streptomycin (Roche) and Glutamax (Life Technologies). After 7 days, 100 µl was replaced with fresh medium supplemented with rh-IL-2 (3,000 IU ml$^{-1}$ final) and T cell specificity was confirmed by assessing IFN-γ in response to neo-epitope after 14 days.

Identification of TCR sequences. cDNA of T cell clones was generated and used to prepare DNA libraries with the Illumina TruSeq DNA library preparation kit. The resulting DNA libraries were sequenced on a Illumina MiSeq sequenzer using Paired-end 150 bp chemistry.

Sequencing reads in FASTQ files were mapped to the human genome, build NCBI36/hg18, using BWA[20] and SAMtools[23]. PCR duplicates in resulting BAM files were filtered using Picard (http://picard.sourceforge.net). CDR3 TCR sequences were identified as previously reported[27]. TCRα and −β sequences were conferred with an in-house developed python script.

Statistical analysis. Differences in cytokine concentrations and frequencies of cytokine-producing T were compared using a two-tailed Student's t test. P values<0.05 were considered significant; Significance was indicated as P<0.05 (*), P<0.01 () and P<0.001 (*).

Results

Tumor-specific neo-antigens arising as a consequence of mutations in human cancers[1,2] are thought to be important for the efficacy of clinically used cancer immunotherapies[3-5]. While tumor-specific CD4+ T cell responses are known and growing evidence suggests that neo-antigens may be commonly recognized by intratumoral CD8+ T cells[3,4,6], it is unknown whether neo-antigen specific CD4+ T cells commonly reside within human tumors. Here, we use immortalized Bcl-6/Bcl-xL transduced B cells to measure the occurrence of CD4+ T cell responses against putative neo-epitopes that are identified by tumor exome sequencing. Using this approach, we show the presence of neo-antigen reactive CD4+ T cells in 4 out of 5 melanoma patients analyzed, including melanoma patients who demonstrate a clinical response after adoptive T cell therapy.

Based on I) the evidence that supports a role for CD4+ T cells in the efficacy of cancer immunotherapies[7-12], II) the proposed correlation between mutational load and clinical response to immunotherapy[13], and III) the recent observation that neo-antigen specific CD4+ T cells can mediate tumor-regression in a metastatic cholangiocarcinoma[10], we wish to understand whether neo-antigen specific CD4+ T cell reactivity is a rare or common phenomenon in human cancers.

The average mutational load of melanoma is high[1]. Furthermore, the tumor-infiltrating lymphocyte (TIL) products that are generated for cellular therapy of melanoma[14] regularly contain substantial fractions of CD4+ T cells, potentially mediating clinical effects[7,10]. Because of these data, we chose to examine the occurrence of neo-antigen specific CD4+ T cell reactivity in a set of melanoma specimens with varying mutational loads.

Figure 1:
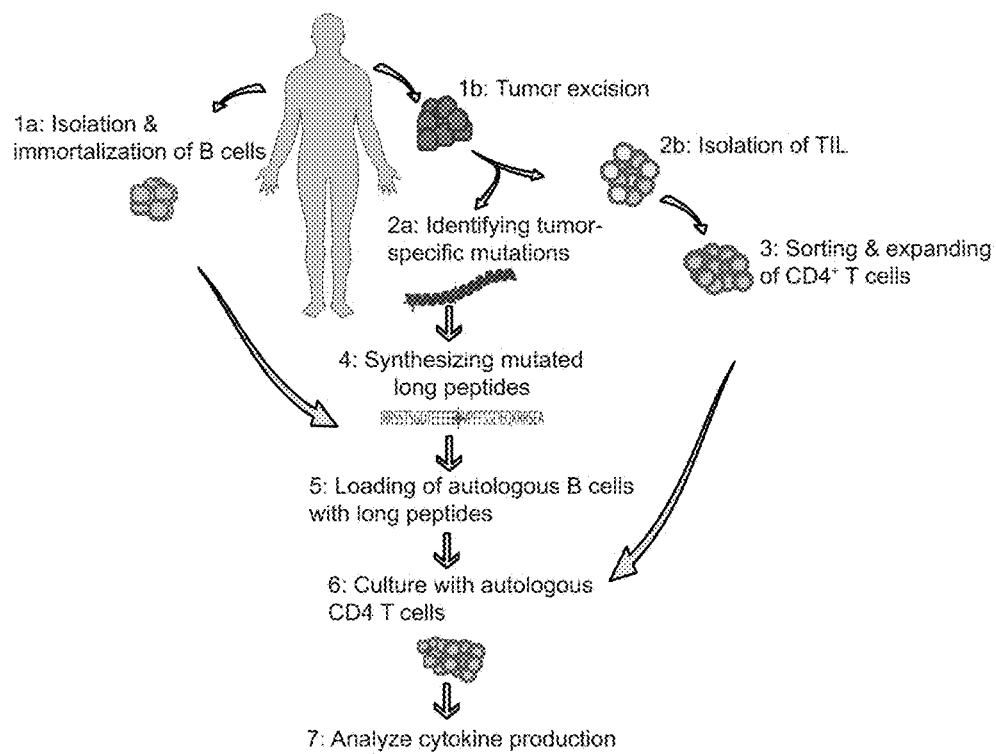
FIG. 1. Experimental setup for the identification of neo-antigen specific CD4+ T cells in tumor lesions. Whole exome-sequencing of tumor and healthy material in combination with RNA-sequencing identifies tumor-specific, non-synonymous mutations within genes with confirmed RNA-expression. This information was used to create a library of putative neo-epitopes comprised of 31 amino-acid long peptides extending each identified mutation by 15 amino-acids on either side.
Autologous B cells immortalized by retroviral gene transfer of Bcl-6 and Bcl-xL enable the profiling of CD4+ T cell reactivity against all MHC-class 11 haplotypes of the subject. Stimulation of CD4+ T cell cells obtained from melanoma lesion of the same subject by neo-antigen peptide-loaded Bcl-6/Bcl-xL immortalized B cells enables the detection of pre-existing CD4+ T cell reactivity with high sensitivity.

To assess the occurrence of intratumoral CD4+ T cell responses against non-synonymous somatic mutations within these tumors, we used whole exome-sequencing and RNA-sequencing data to first identify the entire set of tumor-specific, non-synonymous mutations within expressed genes. Subsequently CD4+ T cell reactivity against any of these mutated peptides was analyzed by the use of retrovirally Bcl-6 and Bcl-xL immortalized autologous B cells[15,16] (see also WO 2007/067046) which were loaded with mutated peptides (FIG. 1).

This screening platform was validated by the analysis of three melanoma lesions—NKIRTIL018. NKIRTIL034 and NKIRTIL045—from patients who underwent palliative metastasectomy. While all three tumors showed the expected UV induced mutational signature, total mutational load varied considerably (range: 180-464 somatic mutations. FIG. 2)[1,2]. On average 153 mutations (Range: 99-187) were identified as candidate neo-epitopes (defined as a tumor-specific, non-synonymous mutation in a gene with confirmed RNA-expression). Peptides (31 amino-acids) that covered the individual mutations were then loaded onto the Bcl-6/Bcl-xL immortalized, autologous B cells, and the resulting targets were incubated with in vitro expanded, intratumoral CD4+ T cells (routinely ≥97% CD4+). Subsequently, we assessed culture supernatants for the presence of the $T_{H1}$, $T_{H2}$ and $T_{H17}$ cytokines IFN-γ, TNF-α, IL-10, IL-2, IL-4, IL-6 and IL-17a. For subject NKIRTIL018, IFN-γ production of tumor-derived CD4+ T cells was observed in response to three mutated gene products. CIRH1A P333L (CIRH1A$_{P>L}$). GART V551A (GART$_{V>A}$), and ASAP1 P941L (ASAP1$_{P>L}$) (FIG. 3a).

Figure 4:
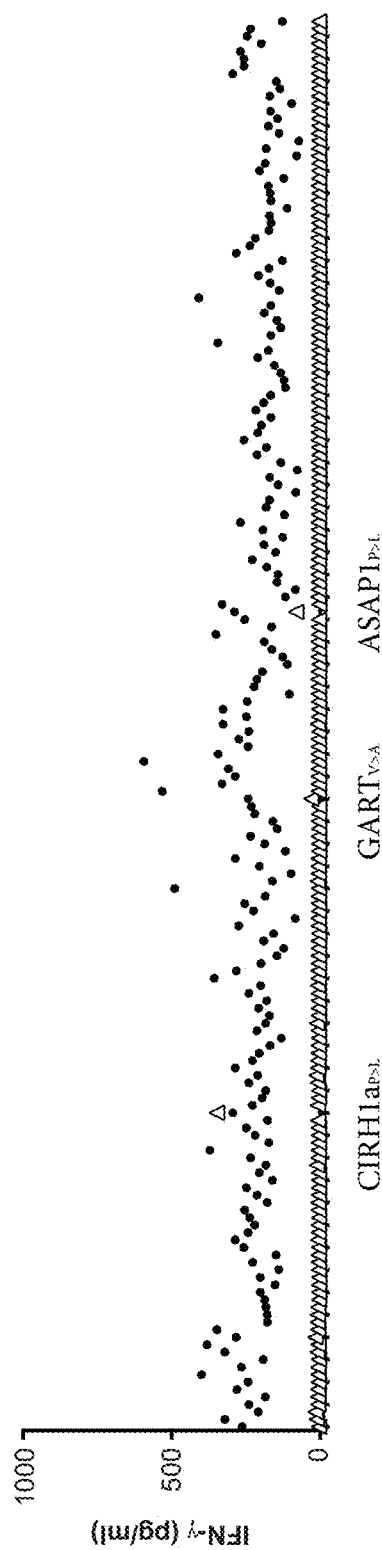
FIG. 4. Detection of neo-epitope specific CD4+ T cells in a melanoma lesion using BCL-6/BCL-XL or Epstein-Barr virus (EBV) immortalized, autologous B cells. IFN-γ concentration in culture supernatant after 48 h co-culture of in vitro expanded intratumoral CD4+ T cells with peptide loaded, autologous B-cells immortalized by stable transfection with BCL-6/BCL-XL (triangles) or EBV infection (circles) derived from NKIRTIL018.

Importantly, detection of these neo-antigen specific CD4+ T cells was readily feasible as a result of the constant low background observed when using autologous Bcl-6/Bcl-xL immortalized B cells. Contrary, detection of these neo-antigen specific CD4+ T cells was impossible with autologous Epstein-Barr virus (EBV) immortalized B cells (FIG. 4).

This demonstrates that the use of Bcl-6/Bcl-xL immortalized B cells is superior over the use of EBV immortalized B cells.

Melanoma-derived CD4+ T cells of subject NKIRTIL034 also showed neo-antigen reactivity, in this case to a mutation within the Rho family GTPase 3 RND P49S (RND3$_{P>S}$). Only in the subject with the lowest mutational load, NKIRTIL027, reactivity against neo-antigens as measured by production of TH-cytokines was not observed within the intratumoral CD4+ T cell compartment (FIG. 3a and data not shown). The presence of neo-antigen reactive CD4+ T cells within the melanoma lesions of NKIRTIL018 and NKIRTIL034 was confirmed by analysis of intracellular IFN-γ levels upon antigen stimulation (FIG. 3b,c). Of note, in this experiment wherein Bcl-6/Bcl-xL immortalized B cells were used, the control frequency of single, live, CD4+, IFN-γ+ T cells after co-culture with unloaded B cells was 0.078% (FIG. 3b) or 0.277% (FIG. 3c). This means that only 0.078% or 0.277% of the CD4+ T cells that were co-cultured with unloaded Bcl-6/Bcl-xL immortalized B cells displayed IFN-γ production (indicative for T cell activation). Importantly, these control frequencies are much lower than the control frequency of 1.98% that was obtained when EBV-immortalized B cells were used (see Example 3 and FIG. 10c).

As shown in FIGS. 3b and 3c, the frequency of the CIRH1a$_{P>L}$-recognizing T cells was 0.096% (i.e. 0.174% minus the control frequency of 0.078%). The frequency of the GART$_{V>A}$-recognizing T cells was 0.053% (i.e. 0.131% minus the control frequency of 0.078%). The frequency of the ASAP1$_{P>L}$-recognizing T cells was 0.264% (i.e. 0.342% minus the control frequency of 0.078%) and the frequency of the RND3$_{P>S}$-recognizing T cells was 0.246% (i.e. 0.523% minus the control frequency of 0.277%). Hence, it is clear that the neo-antigen recognizing T cells were present in very low frequencies. Nevertheless, they could still be detected, thanks to the very sensitive screening methods according to the present invention wherein Bcl-6/Bcl-xL immortalized B cells are used for T cell neo-antigen presentation. These T cells could not have been detected using EBV-immortalized B cells as antigen presenting cells.

Figure 5A:
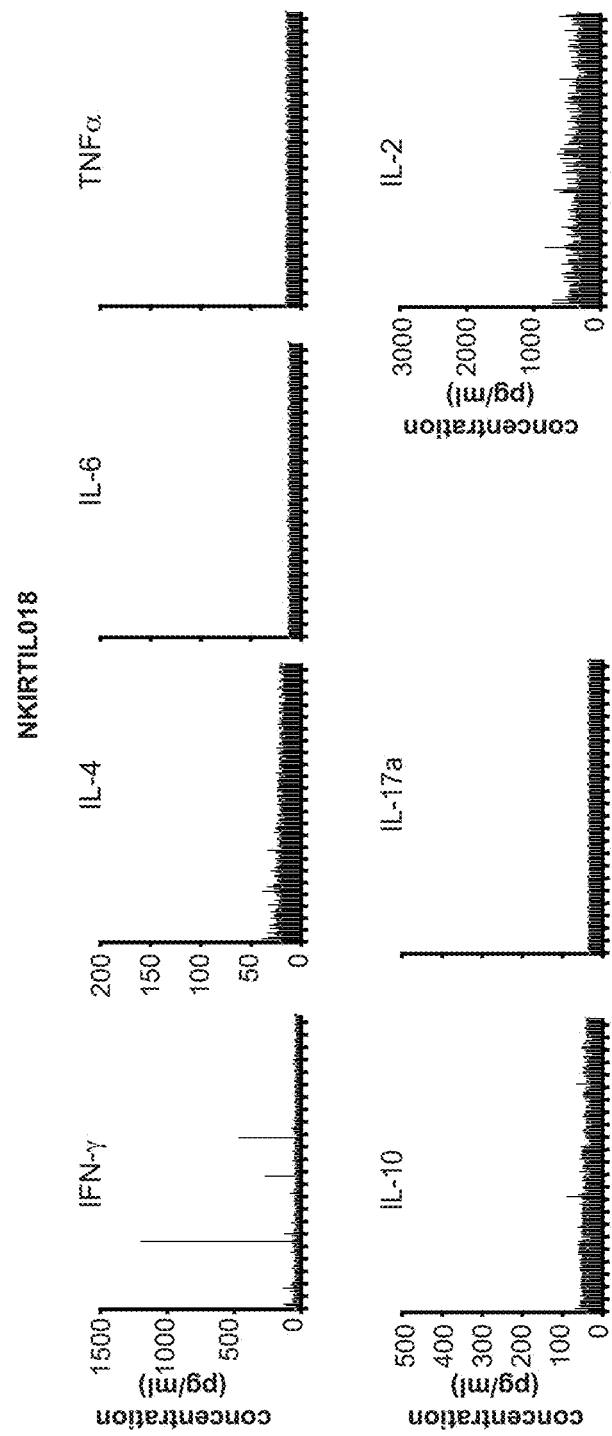
FIG. 5. Detection of T$_{H1}$, T$_{H2}$ and T$_{H17}$ cytokines by intratumoral CD4+ T cells in response to putative neo-epitopes. Cytokine concentration in culture supernatant after 48 h co-culture of peptide loaded, autologous B-cells with in vitro expanded intratumoral CD4+ T cells from (a)
Figure 5B:
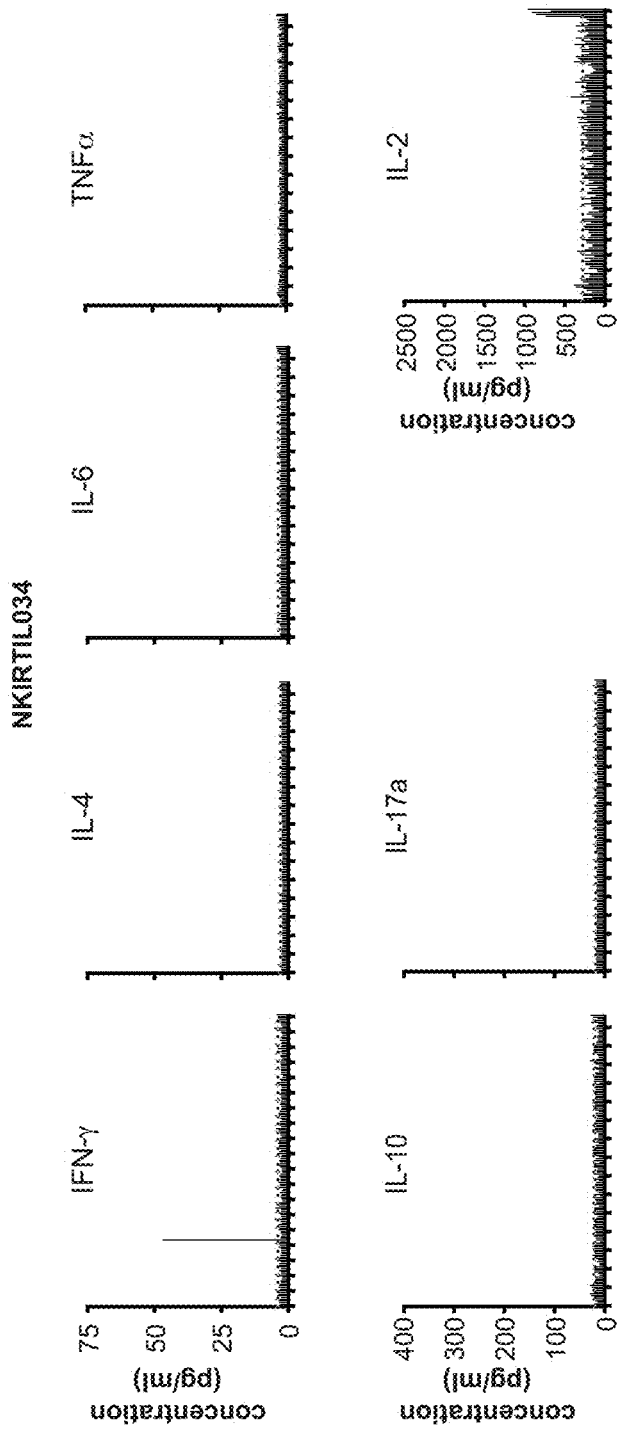

Neo-antigen reactive CD4+ T cells did not show production of any of the other cytokines tested (FIG. 5).

T cell receptors can trigger T cell function upon interaction with a large number of different epitopes, and in the above screens, a diverse T cell pool is tested for recognition of a sizable set of peptides. Thus, we assessed in a set of validation screens whether the observed T cell reactivity represented a genuine neo-antigen driven T cell response, rather than T cell cross reactivity. In these screens, the ability of CD4+ T cell pools from NKIRTIL018 and NKIRTIL034 to react against the set of potential neo-epitopes of the other subject was evaluated. This analysis showed that IFN-γ production by tumor-derived CD4+ T cells was patient mutanome specific as none of the other subject's neo-epitopes were recognized (FIG. 6), indicating that the presence of CD4+ T cells with neo-antigen reactivity identified through the use of Bcl-6/Bcl-xL immortalized B cells reflects a true neo-antigen specific CD4+ T cell response, driven by expression of the antigen in the autologous melanoma.

In order to further characterize the neo-antigen reactive CD4, T cell compartment in these melanoma patients, we generated a panel of neo-epitope reactive CD4+ T cell clones from TIL by isolation of antigen-specific IFN-γ producing CD4+ T cells (FIG. 7+8). To assess the capacity of neo-antigen reactive CD4+ T cells to discriminate between the mutated cognate peptide and its parental sequence, neo-antigen specific CD4+ T cells were stimulated with different concentrations of either peptide (FIG. 7c+FIG. 9). For all T cell clones, specific for either ASAP1$_{P>L}$, CIRH1A$_{P>L}$, or GART$_{V>A}$, recognition of the mutant peptide was detectable at concentrations that were ~100 to >1,000 lower than that required for recognition of the parental peptide (FIG. 7c+FIG. 9). Thus, both by their restriction towards the autologous mutanome set and by their preferential recognition of the mutant peptide over its wild-type counterpart, these tumor-resident CD4+ T cell responses are defined as true neo-antigen driven T cell reactivities.

Truncation of two of the identified neo-epitopes revealed that peptides of 13 amino acids (RKITFLIIRCLISC; CIRH1$_{P>L}$) and 19 amino acids (KPPPGDLP LKPTELAPKPQ; ASAP1$_{P>L}$) were still recognized with high efficiency (FIG. 7c). For both epitopes, the mutated residue was located at a central position within truncated epitope, consistent with an essential role of this amino acid in T cell activation[17,18]. For each of the four identified neo-epitopes, TCR alpha-beta sequences were obtained for a small set (8-11) of T cell clones. This analysis demonstrated that the TCR repertoire of neo-epitope specific T cell responses is generally oligoclonal to polyclonal, with 2-7 identified TCR clonotypes for these 4 epitopes (FIG. 7b). Hence, the neo-antigen specific T cell responses towards these 4 epitopes are not due to the outgrowth of rare neo-antigen reactive CD4+ T cells but are oligo- to polyclonal.

Example 2

Based on the observation that neo-antigen specific CD4+ T cell reactivity can readily be detected on the basis of cancer exome data (FIG. 3), and that a T cell product containing a high frequency of neo-antigen specific CD4+ T cells was recently shown to mediate partial regression of a cholangiocarcinoma[10], we analyzed whether a neo-antigen reactive CD4+ T cell compartment is also prevalent in melanoma patients who experience a clinical response upon adoptive T cell therapy.

The first patient, NKIRTIL027, was a stage IV melanoma patient who exhibited a partial clinical response upon TIL therapy. Exome sequencing revealed a very high mutational burden in the tumor of this patient (total of 1393 somatic mutations) (FIG. 2). Bcl-6/Bcl-xL transduced B cells were loaded with the collection of 582 candidate neo-epitopes, identified after filtering for non-synonymous and RNA expressed mutations, and used as targets for CD4+ T cells expanded from an autologous melanoma lesion. Strikingly, this analysis identified CD4+ T cell reactivity against 7 different mutated gene products (CPT1A G212S (CPT1A$_{G>S}$), HERC4 P768S (HERC4$_{P>S}$). GYLTL1B D597E (GYLTL1B$_{D>E}$), KRTAP4-11 P187S (KRTAP4-11$_{P>S}$), LEMD2 P495L (LEMD2$_{P>L}$), DTNBP1 D334H (DTNBP1$_{D>H}$), MFSD9 P219L (MFSD9$_{P>L}$) as detected by IFN-γ production in culture supernatants and independent confirmation by intracellular detection of IFN-γ production. In particular, this analysis identified strong CD4+ T cell reactivity against the mutated gene product LEM Domain Containing 2 P495, (LEMD2$_{P>L}$), as detected by IFNγ secretion (FIG. 10a).

Of note, the T cell product infused into subject NKIRTIL027 contained a substantial fraction of CD4+ T cells (70% of all CD3+ T cells; data not shown). Thus, we assessed the frequency of neo-antigen reactive CD4+ T cells within the T cell product used for adoptive T cell therapy. This analysis revealed the presence of 7 different neo-epitope reactive CD4+ T cell populations within the infusion cell product with an average frequency of 2.9% (Range: 1.7-4.5%) of total CD4+ T cells. FIG. 10b depicts LEMD2$_{P>L}$ reactive CD4+ T cells (3.8% of total CD4+ T cells) that were observed within the T cell product used for adoptive T cell therapy by intracellular cytokine staining.

Of note, also in this experiment wherein Bcl-6/Bcl-xL immortalized B cells were used, the control frequencies of single, live, CD4+, IFN-γ+ T cells after co-culture with unloaded B cells were 0.52% (In vitro expanded intratumoral CD4+ T cells from an autologous melanoma lesion) and 0.20% (TIL infusion product used for adoptive T cell therapy); see FIG. 10b. Importantly, these control frequencies are much lower than the control frequency of 1.98% that was obtained when EBV-immortalized B cells were used (see Example 3 and FIG. 10c).

The frequency of the LEMD2$_{P>L}$-recognizing T cells in the in vitro expanded intratumoral CD4+ T cells was 4.74% (i.e. 5.26% minus the control frequency of 0.52%). The frequency of the LEMD2$_{P>L}$-recognizing T cells in the TIL infusion product used for adoptive T cell therapy was 3.33% (i.e. 3.53% minus the control frequency of 0.20%).

Example 3

Next, we analyzed neo-antigen specific CD4+ T cell reactivity in a stage IV melanoma patient (BO) who received multiple infusions of in vitro expanded, autologous tumor-specific T cells obtained by stimulation of peripheral blood mononuclear cells (PBMCs) with autologous tumor cells (ref 19). Following treatment, this patient experienced a complete tumor remission, now ongoing for 7 years. Furthermore. CD4+ T cells present within the T cell product showed strong recognition of the autologous melanoma line (FIG. 10c). As Bcl-6/Bcl-xL immortalized B cells were not yet available for this subject, autologous EBV-immortalized B cells had to be used in spite of the larger background noise. The EBV-immortalized B cells were loaded with 31-mer peptides covering the 501 non-synonymous mutations within expressed genes that were detected in this patient. In spite of the higher background noise due to the use of EBV-transformed APCs, this screen identified one prominent CD4+ T cell response (24% of total CD4+ T cells within the infusion product; i.e. 26.0% minus the control frequency of 1.98%) that was directed against a mutant version of ribosomal protein S12 (RPS12 V104I) (FIG. 10c).

Of note, in this experiment wherein EBV-immortalized B cells were used, the control frequency of single, live, CD4+, IFN-γ+ T cells after co-culture with unloaded B cells, is 1.98%. This means that 1.98% of the CD4+ T cells that were co-cultured with unloaded EBV-immortalized B cells displayed IFN-γ production (indicative for T cell activation). Importantly, this control frequency is much higher than the frequencies of each of the four neo-epitope-specific T cells that were found in Example 1. As shown in FIGS. 3b and 3c, the frequency of the CIRH1a$_{P>L}$-recognizing T cells was 0.096% (i.e. 0.174% minus the control frequency of 0.078%). The frequency of the GART$_{V>A}$-recognizing T cells was 0.053% (i.e. 0.131% minus the control frequency of 0.078%). The frequency of the ASAP1$_{P>L}$-recognizing T cells was 0.264% (i.e. 0.342% minus the control frequency of 0.078%) and the frequency of the RND3$_{P>S}$-recognizing T cells was 0.246% (i.e. 0.523% minus the control frequency of 0.277%). It is clear that these low concentrations of neo-epitope-specific T cells would not have been detected using EBV-immortalized B cells in view of the much higher background noise that is present when EBV-immortalized B cells are used. Hence, if EBV-immortalized B cells were used as APCs, all four neo-epitope specific T cells identified in Example 1 would have been missed. This emphasizes the superiority of the use of Bcl-6/Bcl-xL immortalized B cells as T cell (neo)epitope presenting APCs.

Conclusion

The above data show that B cells that are immortalized with a method according to WO 2007/067046 are preferred APCs for testing T cell recognition of T cell epitopes. As shown in Examples 1 and 2, the use of Bcl-6/Bcl-xL immortalized B cells is superior over the use of EBV immortalized B cells, because EBV immortalized B cells provide high levels of background noise. Contrary, when Bcl-6/Bcl-xL immortalized B cells are used as APCs, background noise is much lower, if present at all. This is for instance shown in FIG. 4.

Figure 3:
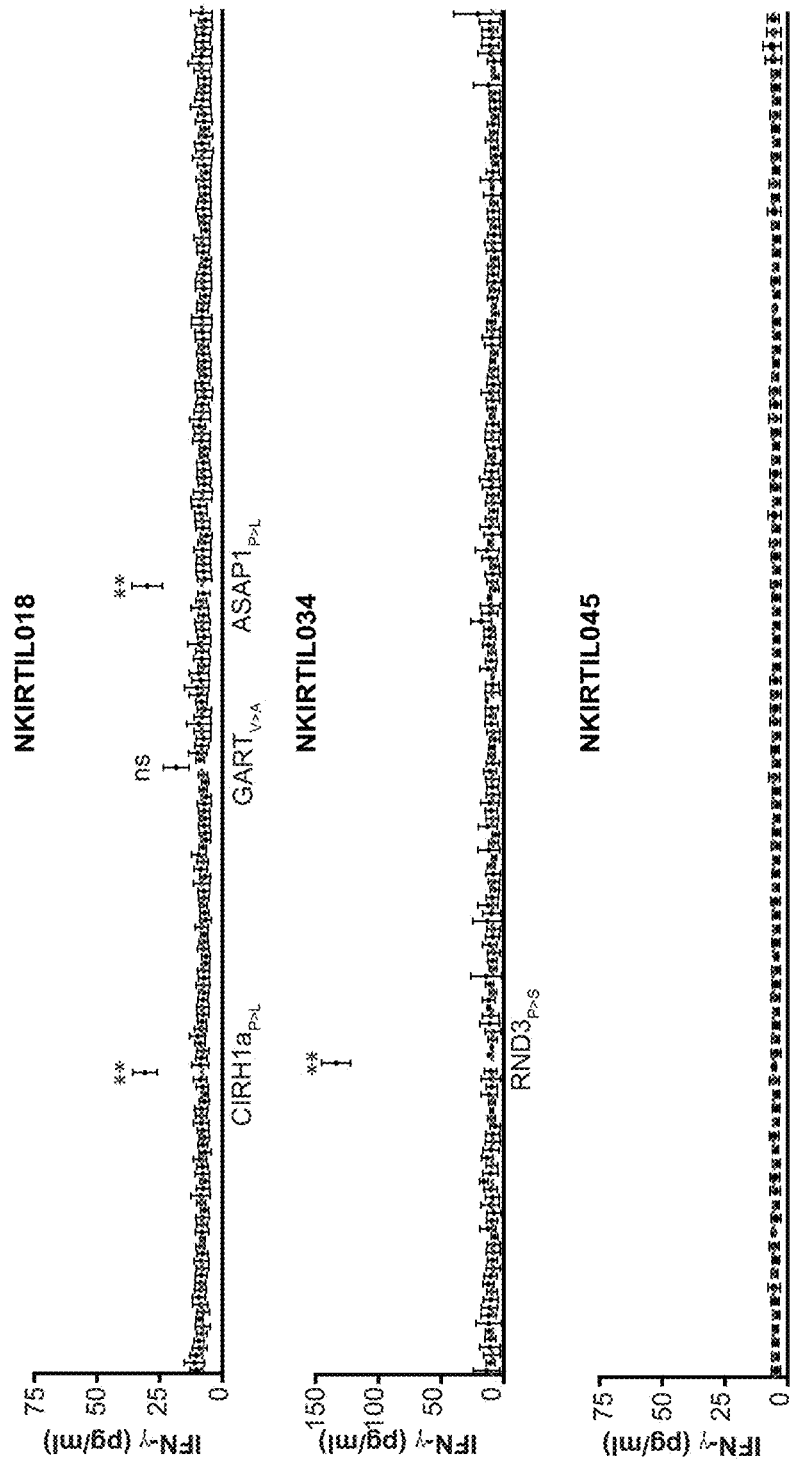
FIG. 3. Detection of neo-epitope specific CD4+ T cells in human melanoma lesions. (a) Mean IFN-γ concentration in culture supernatant after 48 h co-culture of peptide loaded, autologous B-cells with in vitro expanded intratumoral CD4, T cells (n=2-3). Dotted line indicates mean IFN-γ production of CD4+ T cells after co-culture with unloaded B-cells. Error bars depict s.d. CIRH1$_{P>L}$ P=0.0026. GART$_{V>A}$ P=0.0645. ASAP1$_{P>L}$ P=0.0063, RND3$_{P>S}$ P=0.0061. (b,c) Detection of intracellular IFN-γ levels 24 h after co-culture of peptide loaded autologous B-cells with in vitro expanded, intratumoral CD4+ T cells for (b) NKIRTIL018 and (c) NKIRTIL034. Flow cytometry plots depicting single, live, CD4+, T cells from a representative experiment. Controls indicate frequency of single, live, CD4+, IFN-γ+ T cells after co-culture with unloaded B-cells. Bar graphs depict mean IFN-γ concentration over multiple experiments (n=3). Error bars depict s.d. CIRH1$_{P>L}$ P<0.0001, GART$_{V>A}$ P=0.0028. ASAP1$_{P>L}$ P=0.0012, RND3$_{P>S}$ P=0.037.
Figure 3:
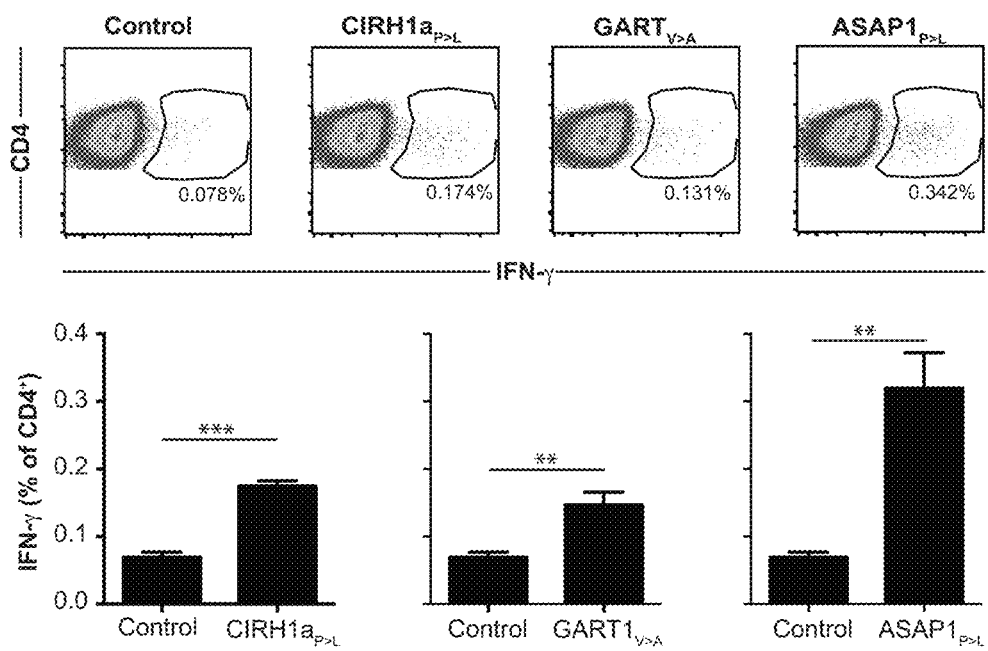
Figure 3:
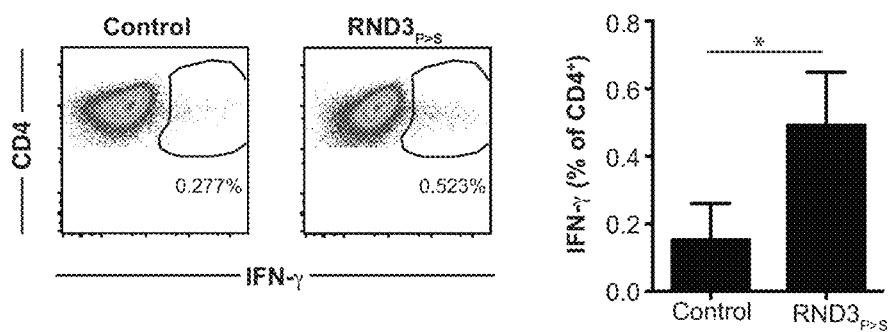

This is also apparent from a comparison between the low control frequencies of FIGS. 3b and 3c, obtained with the use of Bcl-6/Bcl-xL immortalized B cells as APCs (0.078% and 0.277%, respectively) and the high control frequency of FIG. 10, obtained with the use of EBV-immortalized B cells as APCs (1.98%). In fact, the control frequency of FIG. 10 is much higher that the frequencies of the neo-epitope-specific T cells depicted in FIG. 3.

As a consequence, a more sensitive detection method is provided by the present invention, which enables detection of T cells which are present in low frequencies. For instance, 7 different neo-epitope reactive CD4+ T cell populations with an average frequency of 2.9% of total CD4+ T cells were identified in Example 1, using Bcl-6/Bcl-xL immortalized B cells as APCs. With EBV immortalized B cells, only one prominent CD4+ T cell response with a much higher frequency of 24% of total CD4+ T cells was detected (i.e. 26.0% minus the control frequency of 1.98%).

Example 4

Detection of Neo-Epitope Specific CD8+ T Cells in a Human Melanoma Lesion.

This Example shows that the use of Bcl-6/Bcl-xL immortalized B cells as APCs, as described in the previous Examples for the identification of neo-epitope specific CD4+ T cell responses, is also suitable to identify neo-epitope specific CD8+ T cell responses.

Based on exome- and RNA sequencing data of patient NKIRTIL027 (see Example 2), 582 tumor-specific single nucleotide variants were identified with RNA expression>0 FPKM. 31 amino acid peptides covering these mutations were synthesized and loaded on Bcl-6/Bcl-xL immortalized autologous B cells. A 48 co-culture with CD8 enriched tumor infiltrating T cells (TIL) was performed and IFNg concentration was measured in the culture supernatant. Incubation of CD8 enriched TIl with one peptide (TTC37$_{A>V}$) resulted in a signal above background (i.e. above the control signals of unloaded B cells). This is shown in FIG. 11a. As a validation of this result, an independent co-culture in which IFNg concentration was measured in the culture supernatant was performed (FIG. 11b). In parallel, epitope predictions were performed in which the 31 AA epitope was fed into netMHCpan to test for affinity to the patient's HLA-A and HLA-B alleles. A putative candidate undecamer epitope was predicted to bind to HLA-A*01:01. HLA-A*01:01 TTC37$_{A>V}$ multimers were generated and conjugated to two different fluorochromes. Staining of the CD8+ enriched T cell product resulted in a double positive multimer staining of 0.737% of all CD8+ T cells (FIG. 11c).

The applicability of the use of Bcl-6/Bcl-xL immortalized B cells as APCs for both screening neo-epitope specific CD8 and CD4 restricted T cell responses greatly increases the value of this analytic platform in the field of cancer immunotherapy.

REFERENCES OF EXAMPLES 1-4

1. Alexandrov, L. B., et al. Signatures of mutational processes in human cancer. *Nature* 500, 415-421 (2013).
2. Vogelstein. B., et al. Cancer genome landscapes. *Science* 339, 1546-1558 (2013).
3. Robbins, P. F., et al. Mining exomic sequencing data to identify mutated antigens recognized by adoptively transferred tumor-reactive T cells. *Nature medicine* 19, 747-752 (2013).
4. van Rooij, N., et al. Tumor exome analysis reveals neoantigen-specific T-cell reactivity in an ipilimumab-responsive melanoma. *Journal of clinical oncology: official journal of the American. Society of Clinical Oncology* 31, e439-442 (2013).
5. Lu, Y. C., et al. Mutated PPP1R3B is recognized by T cells used to treat a melanoma patient who experienced a durable complete tumor regression. *J Immunol* 190, 6034-6042 (2013).
6. Wick. D. A., et al. Surveillance of the tumor mutanome by T cells during progression from primary to recurrent ovarian cancer. *Clinical cancer research: an official journal of the American Association for Cancer Research* 20, 1125-1134 (2014).
7. Friedman. K. M., et al. Tumor-specific CD4+ melanoma tumor-infiltrating lymphocytes. *J Immunother* 35, 400-408 (2012).
8. Kitano. S., et al. Enhancement of tumor-reactive cytotoxic CD4(+) T cell responses after ipilimumab treatment in four advanced melanoma patients. *Cancer immunology research* 1(2013).
9. Quezada, S. A., et al. Tumor-reactive CD4(+) T cells develop cytotoxic activity and eradicate large established melanoma after transfer into lymphopenic hosts. *The Journal of experimental medicine* 207, 637-650 (2010).
10. Tran, E., et al. Cancer immunotherapy based on mutation-specific CD4+ T cells in a patient with epithelial cancer. *Science* 344, 641-645 (2014).
11. Kenter. G. G., et al. Vaccination against HPV-16 oncoproteins for vulvar intraepithelial neoplasia. *The New England journal of medicine* 361, 1838-1847 (2009).
12. Ossendorp, F., Mengede. E., Camps, M., Filius, R. & Melief, C. J. Specific T helper cell requirement for optimal induction of cytotoxic T lymphocytes against major histocompatibility complex class II negative tumors. *The Journal of experimental medicine* 187, 693-702 (1998).
13. Champiat, S., Ferte, C., Lebel-Binay. S., Eggermont, A. & Soria. J. C. Exomics and immunogenics: Bridging mutational load and immune checkpoints efficacy. *Oncoimmunology* 3, e27817 (2014).
14. Dudley, M. E., et al. Cancer regression and autoimmunity in patients after clonal repopulation with antitumor lymphocytes. *Science* 298, 850-854 (2002).
15. Kwakkenbos, M. J., et al. Genetic manipulation of B cells for the isolation of rare therapeutic antibodies from the human repertoire. *Methods* 65, 38-43 (2014).

16. Kwakkenbos, M. J., et al. Generation of stable monoclonal antibody-producing B cell receptor-positive human memory B cells by genetic programming. *Nature medicine* 16, 123-128 (2010).
17. Kessels, H. W., et al. The impact of self-tolerance on the polyclonal CD8+ T cell repertoire. *J Immunol* 172, 2324-2331 (2004).
18. Calis. J. J., et al. Properties of MHC class I presented peptides that enhance immunogenicity. *PLoS computational biology* 9, e1003266 (2013).
19. Verdegaal, E. M., et al. Successful treatment of metastatic melanoma by adoptive transfer of blood-derived polyclonal tumor-specific CD4+ and CD8+ T cells in combination with low-dose interferon-alpha. *Cancer immunology, immunotherapy: CII* 60, 953-963 (2011).
20. Li, H. & Durbin, R. Fast and accurate short read alignment with Burrows-Wheeler transform. *Bioinformatics* 25, 1754-1760 (2009).
21. DePristo, M. A., et al. A framework for variation discovery and genotyping using next-generation DNA sequencing data. *Nature genetics* 43, 491-498 (2011).
22. Larson. D. E., et al. SomaticSniper: identification of somatic point mutations in whole genome sequencing data. *Bioinformatics* 28, 311-317 (2012).
23. Li, H., et al. The Sequence Alignment/Map format and SAMtools. *Bioinformatics* 25, 2078-2079 (2009).
24. Cingolani, P., et al. A program for annotating and predicting the effects of single nucleotide polymorphisms, SnpEff: SNPs in the genome of *Drosophila melanogaster* strain w1118; iso-2; iso-3. *Fly* 6, 80-92 (2012).
25. Trapnell. C., Pachter. L. & Salzberg, S. L. TopHat: discovering splice junctions with RNA-Seq. *Bioinformatics* 25, 1105-1111 (2009).
26. Trapnell. C., et al. Transcript assembly and quantification by RNA-Seq reveals unannotated transcripts and isoform switching during cell differentiation. *Nature biotechnology* 28, 511-515 (2010).
27. Linnemann, C., et al. High-throughput identification of antigen-specific TCRs by TCR gene capture. *Nature medicine* 19, 1534-1541 (2013).
28. Varela, I., et al. Exome sequencing identifies frequent mutation of the SWI/SNF complex gene PBRM1 in renal carcinoma. *Nature* 469, 539-542 (2011).

The invention claimed is:

1. A method for determining whether a sample from an individual contains T cells that recognize a tumor-specific T cell epitope or a T cell epitope from an autoantigen or from a pathogen, comprising:
    inducing, enhancing and/or maintaining expression of Bcl-6 and/or STAT5 in at least one B cell;
    inducing, enhancing and/or maintaining expression of an anti-apoptotic nucleic acid in said at least one B cell;
    allowing expansion of said at least one B cell into a B cell culture;
    incubating B cells of said B cell culture with at least one compound comprising said tumor-specific T cell epitope or said T cell epitope from an autoantigen or from a pathogen;
    incubating the resulting B cells with T cells from said sample; and
    determining whether at least one T cell recognizes said tumor-specific T cell epitope or said T cell epitope from an autoantigen or from a pathogen.

2. The method according to claim 1, comprising incubating said B cells with at least one peptide.

3. The method according to claim 1, wherein said at least one peptide has a length of between 5 and 40 amino acids, preferably between 8 and 35 amino acids or between 9 and 31 amino acids.

4. The method according to claim 1, wherein said B cells are incubated with at least 2, preferably with at least 5, preferably with at least 10 different peptides.

5. The method according to claim 1, wherein said T cells comprise CD8+ cytotoxic T cells and/or CD4+ helper T cells.

6. The method according to claim 1, wherein said at least one B cell and said T cells are from the same human individual.

7. The method according to claim 1, herein said T cell epitope is from a modified self-antigen or from a non-self antigen or from an autoantigen.

8. The method according to claim 1, wherein said T cell epitope is a tumor-specific T cell epitope.

9. The method according to claim 8, wherein said tumor is a melanoma or epithelial cancer.

10. The method according to claim 1, wherein said T cell epitope is from a pathogen.

11. The method according to claim 10, wherein said pathogen is a virus, a bacterium or a parasite.

12. The method according to claim 1, wherein said T cell epitope is from an autoantigen.

13. The method according to claim 1, wherein it is determined whether at least one T cell from said sample has recognized at least one of said T cell epitopes by determining whether said at least one T cell is activated.

14. The method according to claim 13, wherein said T cell activation is determined by measuring cytokine release.

15. The method according to claim 1, further comprising preparing a medicament comprising T cells that recognize at least one T cell epitope of said compounds.

16. The method according to claim 1, further comprising identifying at least one T cell epitope recognized by a T cell.

17. The method according to claim 16, further comprising preparing an immunogenic composition, or a prophylactic agent or vaccine, comprising said at least one T cell epitope.

18. The method according to claim 16, further comprising preparing an immunogenic composition, or a prophylactic agent or vaccine, comprising an antigen presenting cell, preferably a B cell, which displays on its surface said at least one T cell epitope.

19. The method according to claim 1, wherein the B cells are incubated with T cells from an individual suffering from, or having suffered from, a disorder.

20. The method according to claim 19, wherein said individual is suffering from, or has suffered from, cancer, preferably melanoma or epithelial cancer.

21. The method according to claim 19, wherein said individual is suffering from, or has suffered from, a pathogen, preferably a virus, a bacterium or a parasite.

22. The method according to claim 19, wherein said individual is suffering from, or has suffered from, an autoimmune disease, preferably multiple sclerosis, diabetes or coeliac disease.

23. The method according to claim 1, wherein said T cells are from a sample from said individual, characterized in that the proportion of T cells specific for a T cell epitope that is associated with said disease, relative to the total amount of T cells, is lower than 10%, more preferably lower than 9%, more preferably lower than 8%, more preferably lower than 7%, more preferably lower than 6%, more preferably lower than 5% in said sample or in a T cell culture after in vitro expansion of said sample.

24. The method according to claim 1, wherein said T cells are from a sample from said individual, characterized in that the proportion of T cells specific for a T cell epitope that is associated with a disorder of interest, relative to the total amount of T cells, is lower than 1.9%, more preferably lower than 1.8%, more preferably lower than 1.7%, more preferably lower than 1.6%, more preferably lower than 1.5% in said sample or in a T cell culture after in vitro expansion of said sample.

25. The method according to claim 1, wherein said T cells are from a sample from said individual, characterized in that the proportion of T cells specific for a T cell epitope that is associated with a disorder of interest, relative to the total amount of T cells, is lower than 1.0%, more preferably lower than 0.9%, more preferably lower than 0.8%, more preferably lower than 0.7%, more preferably lower than 0.6%, more preferably lower than 0.5%, more preferably lower than 0.4%, more preferably lower than 0.3% in said sample or in a T cell culture after in vitro expansion of said sample.

26. The method according to claim 1, wherein a sample from said individual is used, or wherein T cells of a resulting T cell culture after in vitro expansion of said sample are used, wherein the percentage of T cells specific for a T cell epitope that is associated with said disease, relative to the total number of T cells in said sample or in said resulting in vitro T cell culture, is lower than 10%, more preferably lower than 9%, more preferably lower than 8%, more preferably lower than 7%, more preferably lower than 6%, more preferably lower than 5%.

27. The method according to claim 1, wherein a sample from said individual is used, or wherein T cells of a resulting T cell culture after in vitro expansion of said sample are used, wherein the percentage of T cells specific for a T cell epitope that is associated with a disorder of interest, relative to the total number of T cells in said sample or in said resulting in vitro T cell culture, is lower than 1.9%, more preferably lower than 1.8%, more preferably lower than 1.7%, more preferably lower than 1.6%, more preferably lower than 1.5%.

28. The method according to claim 1, wherein a sample from said individual is used, or wherein T cells of a resulting T cell culture after in vitro expansion of said sample are used, wherein the percentage of T cells specific for a T cell epitope that is associated with a disorder of interest, relative to the total number of T cells in said sample or in said resulting in vitro T cell culture, is lower than 1.0%, more preferably lower than 0.9%, more preferably lower than 0.8%, more preferably lower than 0.7%, more preferably lower than 0.6%, more preferably lower than 0.5%, more preferably lower than 0.4%, more preferably lower than 0.3%.

29. The method according to claim 23, wherein said disease or said disorder is selected from the group consisting of cancer, preferably melanoma or epithelial cancer, an infectious disease, preferably a viral infection, a bacterial infection or a parasite infection, and an autoimmune disease, preferably multiple sclerosis, diabetes or coeliac disease.

30. The method according to claim 1, wherein said anti-apoptotic nucleic acid comprises a gene encoding an anti-apoptotic molecule, preferably of the BCL2 family, preferably Bcl-xL, Mcl-1, Bcl-2, A1, Bcl-w, Bcl2L10, or a functional part or homologue thereof, most preferably Bcl-xL or Mcl 1.

* * * * *